US008673927B2

(12) United States Patent
Dugi et al.

(10) Patent No.: US 8,673,927 B2
(45) Date of Patent: *Mar. 18, 2014

(54) USES OF DPP-IV INHIBITORS

(75) Inventors: Klaus Dugi, Dresden (DE); Frank Himmelsbach, Mittelbiberach (DE); Michael Mark, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 111 days.

This patent is subject to a terminal disclaimer.

(21) Appl. No.: 12/946,193

(22) Filed: Nov. 15, 2010

(65) Prior Publication Data

US 2011/0065731 A1 Mar. 17, 2011

Related U.S. Application Data

(63) Continuation of application No. 11/744,703, filed on May 4, 2007, now Pat. No. 8,232,281.

(30) Foreign Application Priority Data

May 4, 2006 (EP) .................................. 06009203

(51) Int. Cl.
*A61K 31/52* (2006.01)
*A61K 31/155* (2006.01)

(52) U.S. Cl.
USPC ................... 514/263.21; 514/635; 514/868

(58) Field of Classification Search
USPC .................................. 514/263.21, 635, 866
See application file for complete search history.

(56) References Cited

U.S. PATENT DOCUMENTS

| | | |
|---|---|---|
| 2,056,046 A | 9/1936 | Fourneau |
| 2,375,138 A | 5/1945 | Victors |
| 2,629,736 A | 2/1953 | Krimmel |
| 2,730,544 A | 1/1956 | Sahyun |
| 2,750,387 A | 6/1956 | Krimmel |
| 2,928,833 A | 3/1960 | Leake et al. |
| 3,174,901 A | 3/1965 | Sterne |
| 3,236,891 A | 2/1966 | Seemuller |
| 3,454,635 A | 7/1969 | Muth |
| 3,673,241 A | 6/1972 | Marxer |
| 3,925,357 A | 12/1975 | Okada et al. |
| 4,005,208 A | 1/1977 | Bender et al. |
| 4,061,753 A | 12/1977 | Bodor et al. |
| 4,599,338 A | 7/1986 | Regnier et al. |
| 4,639,436 A | 1/1987 | Junge et al. |
| 4,687,777 A | 8/1987 | Meguro et al. |
| 4,816,455 A | 3/1989 | Schickaneder et al. |
| 4,873,330 A | 10/1989 | Lindholm |
| 4,968,672 A | 11/1990 | Jacobson et al. |
| 5,041,448 A | 8/1991 | Janssens et al. |
| 5,051,517 A | 9/1991 | Findeisen et al. |
| 5,084,460 A | 1/1992 | Munson, Jr. et al. |
| 5,219,870 A | 6/1993 | Kim |
| 5,223,499 A | 6/1993 | Greenlee et al. |
| 5,234,897 A | 8/1993 | Findeisen et al. |
| 5,258,380 A | 11/1993 | Janssens et al. |
| 5,266,555 A | 11/1993 | Findeisen et al. |
| 5,273,995 A | 12/1993 | Roth |
| 5,284,967 A | 2/1994 | Macher |
| 5,300,298 A | 4/1994 | LaNoue |
| 5,329,025 A | 7/1994 | Wong et al. |
| 5,332,744 A | 7/1994 | Chakravarty et al. |
| 5,389,642 A | 2/1995 | Dorsch et al. |
| 5,399,578 A | 3/1995 | Buhlmayer et al. |
| 5,407,929 A | 4/1995 | Takahashi et al. |
| 5,470,579 A | 11/1995 | Bonte et al. |
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,719,279 A | 2/1998 | Kufner-Muhl et al. |
| 5,728,849 A | 3/1998 | Bouchard et al. |
| 5,753,635 A | 5/1998 | Buckman et al. |
| 5,830,908 A | 11/1998 | Grunenberg et al. |
| 5,958,951 A | 9/1999 | Ahrndt et al. |
| 5,965,555 A | 10/1999 | Gebert et al. |
| 5,965,592 A | 10/1999 | Buhlmayer et al. |
| 6,011,049 A | 1/2000 | Whitcomb |
| 6,107,302 A | 8/2000 | Carter et al. |
| 6,166,063 A | 12/2000 | Villhauer |

(Continued)

FOREIGN PATENT DOCUMENTS

AU 2003280680 A1 6/2004
AU 2009224546 A1 9/2009

(Continued)

OTHER PUBLICATIONS

Bastin, R.J. et al., "Salt Selection and Optimization Procedures for Pharmaceutical New Chemical Entities". Organic Process Research and Development, 2000, vol. 4, p. 427-435.
Chemical Abstract: No. 211513-37-0—Dalcetrapib. "Propanethioic acid, 2-methyl-,S-(2-[[[1-(2-ethylbutyl)cyclohexyl]carbonyl] amino}pheyl}ester". Formula: C23 H35 N O2 S. American Chemical Society. Sep. 20, 1998.
Chemical Abstract: No. 875446-37-0—Anacetrapib. "2-Oxazolidinone, 5-[3,5-bis(trifluoromethyl)phenyl]-3[[4'fluoro-2'-methoxy-5'-(1-methylethyl)-4-(trifluoromethyl)[1,1'-biphenyl]-2-yl]methyl]-4-methyl-,(4S,5R)-" Formula: C30 H25 F10 N O3. American Chemical Society, Feb. 28, 2006.

(Continued)

*Primary Examiner* — Kevin E Weddington
(74) *Attorney, Agent, or Firm* — Michael P. Morris; David L. Kershner

(57) ABSTRACT

The specification describes the use of selected DPP IV inhibitors for the treatment of physiological functional disorders and for reducing the risk of the occurrence of such functional disorders in at-risk patient groups. In addition, the use of the above-mentioned DPP IV inhibitors in conjunction with other active substances is described, by means of which improved treatment outcomes can be achieved. These applications may be used to prepare corresponding medicaments.

26 Claims, No Drawings

(56) References Cited

U.S. PATENT DOCUMENTS

| | | |
|---|---|---|
| 6,248,758 B1 | 6/2001 | Klokkers et al. |
| 6,303,661 B1 | 10/2001 | Demuth et al. |
| 6,342,601 B1 | 1/2002 | Bantick et al. |
| 6,372,940 B1 | 4/2002 | Cavazza |
| 6,548,481 B1 | 4/2003 | Demuth et al. |
| 6,579,868 B1 | 6/2003 | Asano et al. |
| 6,727,261 B2 | 4/2004 | Gobbi et al. |
| 6,784,195 B2 | 8/2004 | Hale et al. |
| 6,821,978 B2 | 11/2004 | Chackalamannil et al. |
| 6,869,947 B2 | 3/2005 | Kanstrup et al. |
| 6,995,183 B2 | 2/2006 | Hamann et al. |
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,074,923 B2 | 7/2006 | Dahanukar et al. |
| 7,109,192 B2 | 9/2006 | Hauel et al. |
| 7,179,809 B2 | 2/2007 | Eckhardt et al. |
| 7,183,280 B2 | 2/2007 | Himmelsbach et al. |
| 7,192,952 B2 | 3/2007 | Kanstrup et al. |
| 7,217,711 B2 | 5/2007 | Eckhardt et al. |
| 7,235,538 B2 | 6/2007 | Kanstrup et al. |
| 7,291,642 B2 | 11/2007 | Kauffmann-Hefner et al. |
| 7,361,687 B2 | 4/2008 | Barth et al. |
| 7,393,847 B2 | 7/2008 | Eckhardt et al. |
| 7,407,955 B2 | 8/2008 | Himmelsbach et al. |
| 7,432,262 B2 | 10/2008 | Eckhardt et al. |
| 7,439,370 B2 | 10/2008 | Eckhardt |
| 7,470,716 B2 | 12/2008 | Eckhardt et al. |
| 7,476,671 B2 | 1/2009 | Eckhardt et al. |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,610,153 B2 | 10/2009 | Carter, Jr. et al. |
| 7,645,763 B2 | 1/2010 | Himmelsbach et al. |
| 7,718,666 B2 | 5/2010 | Boehringer et al. |
| 7,799,782 B2 | 9/2010 | Munson et al. |
| 7,820,815 B2 | 10/2010 | Pfrengle et al. |
| 7,838,529 B2 | 11/2010 | Himmelsbach et al. |
| 8,039,477 B2 | 10/2011 | Hendrix et al. |
| 8,071,583 B2 | 12/2011 | Himmelsbach |
| 8,106,060 B2 | 1/2012 | Pfrengle et al. |
| 8,119,648 B2 * | 2/2012 | Himmelsbach et al. . 514/263.21 |
| 8,158,633 B2 | 4/2012 | Hendrix et al. |
| 8,178,541 B2 * | 5/2012 | Himmelsbach et al. . 514/263.21 |
| 8,232,281 B2 * | 7/2012 | Dugi et al. ............. 514/263.21 |
| 2001/0020006 A1 | 9/2001 | Demuth et al. |
| 2001/0051646 A1 | 12/2001 | Demuth et al. |
| 2002/0019411 A1 | 2/2002 | Robl et al. |
| 2002/0137903 A1 | 9/2002 | Ellsworth et al. |
| 2002/0161001 A1 | 10/2002 | Kanstrup et al. |
| 2002/0169174 A1 | 11/2002 | Chackalamannil et al. |
| 2002/0198205 A1 | 12/2002 | Himmelsbach et al. |
| 2003/0078269 A1 | 4/2003 | Pearson et al. |
| 2003/0100563 A1 | 5/2003 | Edmondson et al. |
| 2003/0105077 A1 | 6/2003 | Kanstrup et al. |
| 2003/0114390 A1 | 6/2003 | Washburn et al. |
| 2003/0149071 A1 | 8/2003 | Gobbi et al. |
| 2003/0166578 A1 | 9/2003 | Arch et al. |
| 2003/0199528 A1 | 10/2003 | Kanstrup et al. |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0023981 A1 | 2/2004 | Ren et al. |
| 2004/0034014 A1 | 2/2004 | Kanstrup et al. |
| 2004/0063725 A1 | 4/2004 | Barth et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097510 A1 | 5/2004 | Himmelsbach et al. |
| 2004/0116328 A1 | 6/2004 | Yoshikawa et al. |
| 2004/0122048 A1 | 6/2004 | Benjamin et al. |
| 2004/0122228 A1 | 6/2004 | Maier et al. |
| 2004/0126358 A1 | 7/2004 | Warne et al. |
| 2004/0138214 A1 | 7/2004 | Himmelsbach et al. |
| 2004/0138215 A1 | 7/2004 | Eckhardt et al. |
| 2004/0166125 A1 | 8/2004 | Himmelsbach et al. |
| 2004/0180925 A1 | 9/2004 | Matsuno et al. |
| 2004/0259903 A1 | 12/2004 | Boehringer et al. |
| 2005/0020574 A1 | 1/2005 | Hauel et al. |
| 2005/0026921 A1 | 2/2005 | Eckhardt et al. |
| 2005/0032804 A1 | 2/2005 | Cypes et al. |
| 2005/0070562 A1 | 3/2005 | Jones et al. |
| 2005/0070594 A1 | 3/2005 | Kauschke et al. |
| 2005/0130985 A1 | 6/2005 | Himmelsbach et al. |
| 2005/0143377 A1 | 6/2005 | Himmelsbach et al. |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt et al. |
| 2005/0234108 A1 | 10/2005 | Himmelsbach et al. |
| 2005/0234235 A1 | 10/2005 | Eckhardt et al. |
| 2005/0239778 A1 | 10/2005 | Konetzki et al. |
| 2005/0256310 A1 | 11/2005 | Hulin et al. |
| 2005/0261271 A1 | 11/2005 | Feng et al. |
| 2005/0261352 A1 | 11/2005 | Eckhardt |
| 2005/0266080 A1 | 12/2005 | Desai et al. |
| 2005/0276794 A1 | 12/2005 | Papas et al. |
| 2006/0004074 A1 | 1/2006 | Eckhardt et al. |
| 2006/0039974 A1 | 2/2006 | Akiyama et al. |
| 2006/0047125 A1 | 3/2006 | Leonardi et al. |
| 2006/0058323 A1 | 3/2006 | Eckhardt et al. |
| 2006/0063787 A1 | 3/2006 | Yoshikawa et al. |
| 2006/0074058 A1 | 4/2006 | Holmes et al. |
| 2006/0079541 A1 | 4/2006 | Langkopf et al. |
| 2006/0094722 A1 | 5/2006 | Yasuda et al. |
| 2006/0100199 A1 | 5/2006 | Yoshikawa et al. |
| 2006/0106035 A1 | 5/2006 | Hendrix et al. |
| 2006/0111372 A1 | 5/2006 | Hendrix et al. |
| 2006/0111379 A1 | 5/2006 | Guillemont et al. |
| 2006/0142310 A1 | 6/2006 | Pfrengle et al. |
| 2006/0154866 A1 | 7/2006 | Chu et al. |
| 2006/0159746 A1 | 7/2006 | Troup et al. |
| 2006/0173056 A1 | 8/2006 | Kitajima et al. |
| 2006/0205711 A1 | 9/2006 | Himmelsbach et al. |
| 2006/0205943 A1 | 9/2006 | Dahanukar et al. |
| 2006/0247226 A1 | 11/2006 | Himmelsbach et al. |
| 2006/0270668 A1 | 11/2006 | Chew et al. |
| 2006/0270701 A1 | 11/2006 | Kroth et al. |
| 2007/0027168 A1 | 2/2007 | Pfrengle et al. |
| 2007/0060530 A1 | 3/2007 | Christopher et al. |
| 2007/0072803 A1 | 3/2007 | Chu et al. |
| 2007/0072810 A1 | 3/2007 | Asakawa |
| 2007/0088038 A1 | 4/2007 | Eckhardt et al. |
| 2007/0093659 A1 | 4/2007 | Bonfanti et al. |
| 2007/0142383 A1 | 6/2007 | Eckhardt et al. |
| 2007/0185091 A1 | 8/2007 | Himmelsbach et al. |
| 2007/0196472 A1 | 8/2007 | Kiel et al. |
| 2007/0219178 A1 | 9/2007 | Muramoto |
| 2007/0259900 A1 | 11/2007 | Sieger et al. |
| 2007/0259925 A1 | 11/2007 | Boehringer et al. |
| 2007/0259927 A1 | 11/2007 | Suzuki et al. |
| 2007/0281940 A1 | 12/2007 | Dugi et al. |
| 2007/0299076 A1 | 12/2007 | Piotrowski et al. |
| 2008/0039427 A1 | 2/2008 | Ray et al. |
| 2008/0107731 A1 | 5/2008 | Kohlrausch et al. |
| 2008/0108816 A1 | 5/2008 | Zutter |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |
| 2008/0318922 A1 | 12/2008 | Nakahira et al. |
| 2009/0023920 A1 | 1/2009 | Eckhardt |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0136596 A1 | 5/2009 | Munson et al. |
| 2009/0137801 A1 | 5/2009 | Himmelsbach et al. |
| 2009/0149483 A1 | 6/2009 | Nakahira et al. |

(56) References Cited

U.S. PATENT DOCUMENTS

| | | |
|---|---|---|
| 2009/0186086 A1 | 7/2009 | Shankar et al. |
| 2009/0192314 A1 | 7/2009 | Pfrengle et al. |
| 2009/0297470 A1 | 12/2009 | Franz |
| 2009/0301105 A1 | 12/2009 | Loerting |
| 2009/0325926 A1 | 12/2009 | Himmelsbach |
| 2010/0074950 A1 | 3/2010 | Sesha |
| 2010/0092551 A1 | 4/2010 | Nakamura et al. |
| 2010/0173916 A1 | 7/2010 | Himmelsbach et al. |
| 2010/0183531 A1 | 7/2010 | Johncock et al. |
| 2010/0204250 A1 | 8/2010 | Himmelsbach et al. |
| 2011/0009391 A1 | 1/2011 | Braun et al. |
| 2011/0046076 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0053173 A1 | 3/2012 | Banno et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0252782 A1 | 10/2012 | Himmelsbach et al. |
| 2012/0252783 A1 | 10/2012 | Himmelsbach et al. |
| 2012/0296091 A1 | 11/2012 | Sieger et al. |
| 2013/0172244 A1 | 7/2013 | Klein et al. |
| 2013/0184204 A1 | 7/2013 | Pfrengle et al. |
| 2013/0196898 A1 | 8/2013 | Dugi et al. |

FOREIGN PATENT DOCUMENTS

| | | |
|---|---|---|
| CA | 1123437 A1 | 5/1982 |
| CA | 2136288 A1 | 5/1995 |
| CA | 2418656 A1 | 2/2002 |
| CA | 2496249 A1 | 3/2004 |
| CA | 2496325 A1 | 3/2004 |
| CA | 2498423 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2558067 A1 | 10/2005 |
| CA | 2561210 A1 | 10/2005 |
| CA | 2562859 A1 | 11/2005 |
| CA | 2576294 A1 | 3/2006 |
| CA | 2590912 A1 | 6/2006 |
| CA | 2651019 A1 | 11/2007 |
| CA | 2651089 A1 | 11/2007 |
| CN | 101234105 A | 8/2008 |
| DE | 2205815 | 8/1973 |
| DE | 2758025 A1 | 7/1979 |
| DE | 10109021 A1 | 9/2002 |
| DE | 10117803 A1 | 10/2002 |
| DE | 10238243 A1 | 3/2004 |
| DE | 102004019540 A1 | 11/2005 |
| DE | 102004024454 A1 | 12/2005 |
| DE | 102004044221 A1 | 3/2006 |
| DE | 102004054054 A1 | 5/2006 |
| EP | 0023032 A1 | 1/1981 |
| EP | 0149578 A2 | 7/1985 |
| EP | 0223403 A2 | 5/1987 |
| EP | 0237608 A1 | 9/1987 |
| EP | 0248634 A2 | 12/1987 |
| EP | 0389282 A2 | 9/1990 |
| EP | 0399285 A1 | 11/1990 |
| EP | 0400974 A2 | 12/1990 |
| EP | 409281 A1 | 1/1991 |
| EP | 0412358 A1 | 2/1991 |
| EP | 443983 A1 | 8/1991 |
| EP | 0524482 A1 | 1/1993 |
| EP | 0657454 A1 | 6/1995 |
| EP | 0775704 A1 | 5/1997 |
| EP | 0950658 A1 | 10/1999 |
| EP | 1054012 A1 | 11/2000 |
| EP | 1066265 A1 | 1/2001 |
| EP | 1333033 | 8/2003 |
| EP | 1338595 A2 | 8/2003 |
| EP | 1406873 A2 | 4/2004 |
| EP | 1500403 A1 | 1/2005 |
| EP | 1514552 A1 | 3/2005 |
| EP | 1537880 A1 | 6/2005 |
| EP | 1557165 A1 | 7/2005 |
| EP | 1586571 A1 | 10/2005 |
| EP | 1743655 A1 | 1/2007 |
| EP | 1760076 | 3/2007 |
| EP | 1829877 A1 | 9/2007 |
| EP | 1852108 A1 | 11/2007 |
| EP | 2143443 A1 | 1/2010 |
| ES | 385302 A1 | 4/1973 |
| ES | 2256797 T3 | 7/2006 |
| ES | 2263057 T3 | 12/2006 |
| FR | 2707641 A1 | 1/1995 |
| GB | 2084580 A | 4/1982 |
| HU | 9003243 | 5/1990 |
| HU | 9902308 A2 | 7/2000 |
| JP | S374895 A | 6/1962 |
| JP | 770120 | 3/1995 |
| JP | 2000026684 A | 3/2000 |
| JP | 2001213770 A | 8/2001 |
| JP | 2003300977 A | 10/2003 |
| JP | 2006045156 A | 2/2006 |
| JP | 2010053576 A | 3/2010 |
| KR | 20070111099 A | 11/2007 |
| WO | 9107945 A1 | 6/1991 |
| WO | 9205175 A1 | 4/1992 |
| WO | 9219227 A2 | 11/1992 |
| WO | 9402150 A1 | 2/1994 |
| WO | 9403456 A1 | 2/1994 |
| WO | 9532178 A1 | 11/1995 |
| WO | 9609045 A1 | 3/1996 |
| WO | 9636638 A1 | 11/1996 |
| WO | 9723447 A1 | 7/1997 |
| WO | 9723473 A1 | 7/1997 |
| WO | 9746526 A1 | 12/1997 |
| WO | 9807725 | 2/1998 |
| WO | 9811893 A1 | 3/1998 |
| WO | 9818770 A1 | 5/1998 |
| WO | 9822464 A1 | 5/1998 |
| WO | 9828007 A1 | 7/1998 |
| WO | 9840069 A2 | 9/1998 |
| WO | 9856406 A1 | 12/1998 |
| WO | 9929695 A1 | 6/1999 |
| WO | 9950248 A1 | 10/1999 |
| WO | 0073307 A2 | 12/2000 |
| WO | 0107441 A1 | 2/2001 |
| WO | 0140180 A2 | 6/2001 |
| WO | 0152825 A2 | 7/2001 |
| WO | 0152852 A1 | 7/2001 |
| WO | 0168646 A1 | 9/2001 |
| WO | 0177110 A1 | 10/2001 |
| WO | 0197808 A1 | 12/2001 |
| WO | 0202560 A2 | 1/2002 |
| WO | 0214271 A1 | 2/2002 |
| WO | 0224698 A1 | 3/2002 |

(56) References Cited

FOREIGN PATENT DOCUMENTS

| | | |
|---|---|---|
| WO | 02053516 A2 | 7/2002 |
| WO | 02068420 A1 | 9/2002 |
| WO | 03000241 A2 | 1/2003 |
| WO | 03002531 A2 | 1/2003 |
| WO | 03004496 A1 | 1/2003 |
| WO | 03024965 A2 | 3/2003 |
| WO | 03037327 A1 | 5/2003 |
| WO | 03055881 A1 | 7/2003 |
| WO | 03057200 A2 | 7/2003 |
| WO | 03064454 A1 | 8/2003 |
| WO | 03088900 A2 | 10/2003 |
| WO | 03099279 A1 | 12/2003 |
| WO | 03099836 A1 | 12/2003 |
| WO | 03104229 A1 | 12/2003 |
| WO | 03106428 A1 | 12/2003 |
| WO | 2004002924 A1 | 1/2004 |
| WO | 2004011416 A1 | 2/2004 |
| WO | 2004018467 A2 | 3/2004 |
| WO | 2004018468 A2 | 3/2004 |
| WO | 2004018469 A1 | 3/2004 |
| WO | 2004028524 A1 | 4/2004 |
| WO | 2004033455 A1 | 4/2004 |
| WO | 2004035575 A1 | 4/2004 |
| WO | 2004041820 A1 | 5/2004 |
| WO | 2004046148 A1 | 6/2004 |
| WO | 2004048379 A1 | 6/2004 |
| WO | 2004050658 A1 | 6/2004 |
| WO | 2004052362 A1 | 6/2004 |
| WO | 2004058233 A1 | 7/2004 |
| WO | 2004062689 A1 | 7/2004 |
| WO | 2004065380 A | 8/2004 |
| WO | 2004081006 A1 | 9/2004 |
| WO | 2004082402 A1 | 9/2004 |
| WO | 2004096806 A1 | 11/2004 |
| WO | 2004096811 A1 | 11/2004 |
| WO | 2004106279 A2 | 12/2004 |
| WO | 2004108730 A1 | 12/2004 |
| WO | 2004111051 A1 | 12/2004 |
| WO | 2005000846 A1 | 1/2005 |
| WO | 2005000848 A1 | 1/2005 |
| WO | 2005007647 A1 | 1/2005 |
| WO | 2005012288 A1 | 2/2005 |
| WO | 2005023179 A2 | 3/2005 |
| WO | 2005049022 A2 | 6/2005 |
| WO | 2005051950 A1 | 6/2005 |
| WO | 2005058901 A1 | 6/2005 |
| WO | 2005061489 A1 | 7/2005 |
| WO | 2005063750 A1 | 7/2005 |
| WO | 2005082906 A1 | 9/2005 |
| WO | 2005085246 A1 | 9/2005 |
| WO | 2005092870 A1 | 10/2005 |
| WO | 2005092877 A1 | 10/2005 |
| WO | 2005095343 A1 | 10/2005 |
| WO | 2005097798 A | 10/2005 |
| WO | 2005116000 A1 | 12/2005 |
| WO | 2005116014 A1 | 12/2005 |
| WO | 2005117861 A1 | 12/2005 |
| WO | 2005117948 A1 | 12/2005 |
| WO | 2006005613 A1 | 1/2006 |
| WO | 2006027204 A1 | 3/2006 |
| WO | 2006029769 A1 | 3/2006 |
| WO | 2006036664 A1 | 4/2006 |
| WO | 2006040625 A1 | 4/2006 |
| WO | 2006047248 A1 | 5/2006 |
| WO | 2006048209 A1 | 5/2006 |
| WO | 2006048427 A1 | 5/2006 |
| WO | 2006068163 A1 | 6/2006 |
| WO | 2006071078 A1 | 7/2006 |
| WO | 2006076231 A2 | 7/2006 |
| WO | 2006083491 A2 | 8/2006 |
| WO | 2006135693 A2 | 12/2006 |
| WO | 2006137085 A1 | 12/2006 |
| WO | 2007007173 A2 | 1/2007 |
| WO | 2007014886 A1 | 2/2007 |
| WO | 2007014895 A2 | 2/2007 |
| WO | 2007017423 A1 | 2/2007 |
| WO | 2007033350 A1 | 3/2007 |
| WO | 2007035355 A2 | 3/2007 |
| WO | 2007035665 A1 | 3/2007 |
| WO | 2007041053 A2 | 4/2007 |
| WO | 2007071738 | 6/2007 |
| WO | 2007072083 A1 | 6/2007 |
| WO | 2007078726 A2 | 7/2007 |
| WO | 2007093610 A1 | 8/2007 |
| WO | 2007099345 A1 | 9/2007 |
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128761 A2 | 11/2007 |
| WO | 2007135196 A2 | 11/2007 |
| WO | 2007137107 A2 | 11/2007 |
| WO | 2007147185 A1 | 12/2007 |
| WO | 2007148185 A2 | 12/2007 |
| WO | 2007149797 A2 | 12/2007 |
| WO | 2008005569 A2 | 1/2008 |
| WO | 2008005576 A1 | 1/2008 |
| WO | 2008017670 | 2/2008 |
| WO | 2008022267 A2 | 2/2008 |
| WO | 2008055870 A1 | 5/2008 |
| WO | 2008055940 A2 | 5/2008 |
| WO | 2008070692 A2 | 6/2008 |
| WO | 2008081205 A1 | 7/2008 |
| WO | 2008083238 A2 | 7/2008 |
| WO | 2008087198 A1 | 7/2008 |
| WO | 2008093878 A1 | 8/2008 |
| WO | 2008093882 A1 | 8/2008 |
| WO | 2008113000 A1 | 9/2008 |
| WO | 2008131149 A2 | 10/2008 |
| WO | 2009011451 A | 1/2009 |
| WO | 2009022007 A1 | 2/2009 |
| WO | 2009022008 A1 | 2/2009 |
| WO | 2009022010 A1 | 2/2009 |
| WO | 2009024542 A2 | 2/2009 |
| WO | 2009063072 A2 | 5/2009 |
| WO | 2009064399 A1 | 5/2009 |
| WO | 2009099734 A1 | 8/2009 |
| WO | 2009112691 A2 | 9/2009 |
| WO | 2009121945 A2 | 10/2009 |
| WO | 2009123992 A1 | 10/2009 |
| WO | 2009147125 A1 | 12/2009 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A2 | 4/2010 |
| WO | 2010072776 A1 | 7/2010 |
| WO | 2010079197 A1 | 7/2010 |
| WO | 2010086411 A1 | 8/2010 |
| WO | 2010092125 A1 | 8/2010 |
| WO | 2010096384 A2 | 8/2010 |
| WO | 20100092163 A2 | 8/2010 |
| WO | 2010106457 A2 | 9/2010 |
| WO | 2010147768 A1 | 12/2010 |
| WO | 2011039367 A2 | 4/2011 |
| WO | 2011064352 A1 | 6/2011 |
| WO | 2011113947 A1 | 9/2011 |
| WO | 2011138380 A1 | 11/2011 |
| WO | 2011138421 A1 | 11/2011 |
| WO | 2011161161 A1 | 12/2011 |
| WO | 2012065993 A1 | 5/2012 |
| WO | 2013103629 A1 | 7/2013 |

OTHER PUBLICATIONS

Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.

Demuth, H-U. et al., "Type 2 diabetes—Therapy with dipeptidyl peptidase IV inhibitors". Biochimica et Biophysica Acta, vol. 1751(1), 2005, p. 33-44.

Gallwitz, B. "Sitagliptin with Metformin: Profile of a Combination for the Treatment of Type 2 Diabetes". Drugs of Today, Oct. 2007, 43(10), p. 681-689.

(56) References Cited

OTHER PUBLICATIONS

Graefe-Mody, et al; Evaluation of the Potential for Steady-State Pharmacokinetic and Phamacodynamic Interactions Between the DPP-4 Inhibitor Linagliptin and Metformin in Healthy Subjects; Currents Medical Research and Opinion (2009) vol. 25, No. 8 pp. 1963-1972.

He, Y. L. et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.

Hunziker, D. et al, "Inhibitors of DPP IV-recent advances and structural views", Current Topics in Medicinal Chemistry, 2005, vol. 5 issue 16, pp. 1623-1637.

Knorr, M. et al., "Comparison of Direct and Indirect Antioxidant Effects of Linagliptin (BI 1356, Ondero) with other Gliptins—Evidence for Anti-Inflammatory Properties of Linagliptin". Free Radical Biology and medicine, Elsevier Science, U.S. vol. 49, Oct. 23, 2010, p. S197.

Levien,T.L. et al, "New drugs in development for the treatment of diabetes", Diabetes Spectrum, American Diabetes Association, US, vol. 22, No. 2, Jan. 1, 2009, pp. 92-106.

Meece, J. "When Oral Agents Fail: Optimizing Insulin Therapy in the Older Adult". Consultant Pharmacist, The Society, Arlington, VA US. vol. 24, No. Suppl B, Jun. 1, 2009, p. 11-17.

Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.

Sune Negre, J. M. "New Galenic Contributions to Administration Forms". Continued Training for Hospital Pharmacists 3.2. [retrieved on Feb. 23, 2011]. Retrieved from the internet <http://www.ub.es/legmh/capitols/sunyenegre.pdf>.

Thomas, L., "Chronic treatment with the Dipeptidyl Peptidase-4 Inhibitor BI 1356[9R)-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.

Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.

European Search Report for EP 08 15 9141 mailed Apr. 6, 2009 (European counterpart of U.S. Appl. No. 12/143,128).

Uhlig-Laske, B. et al., "Linagliptin, a Potent and Selective DPP-4 Inhibitior, is Safe and Efficacious in Patients with Inadequately Controlled Type 2 Diabetes Despite Metformin Therapy". 535-P Clinical Therapeutics/New Technology—Pharmacologic Treatment of Diabetes or Its Complications, Posters, vol. 58, Jun. 5, 2009, p. A143.

Abstract in English for German DE2205815, 1972.

Abstract in English for German EP0023032, 1981.

Abstract in English, for KR20070111099, Nov. 11, 2007.

Augeri, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.

Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.

Aulinger, B.A. et al., "Ex-4 and the DPP-IV Inhibitor Vildagliptin have Additive Effects to Suppress Food Intake in Rodents". Abstract No. 1545-P, 2008.

Balaban, Y.H.et al., "Dipeptidyl peptidase IV (DDP IV) in NASH patients" Annals of Hepatology, vol. 6, No. 4, Oct. 1, 2007, pp. 242-250, abstract.

Balkan, B. et al, "Inhibition of dipeptidyl peptidase IV with NVP-DPP728 increases plasma GLP-1 (7-36 amide) concentrations and improves oral glucose tolerance in obses Zucker rates". Diabetologia, 1999, 42, p. 1324-1331.

Beljean-Leymarie et al., Hydrazines et hydrazones heterocycliques. IV. Syntheses de derives de l'hydrazine dans la serie des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, pp. 18-193.

Brittain, H.G., "Methods for the Characterization of Polymorphs: X-Ray Powder Diffraction," Polymorphism in Pharmaceutical Solids, 1999, p. 235-238.

Busso et al., "Circulating CD26 is Negatively Associated with Inflammation in Human and Experimental Arthritis," Am. J. Path., vol. 166, No. 2, Feb. 2005, pp. 433-442.

Caira, M.R., "Crystalline polymorphism of organic compounds" Topics in Current Chemistry, Springer, Berlin, vol. 198, 1998, p. 163-208.

Chemical Abstract. EP412358, 1991:185517, Findeisen.

Chemical Abstract: FR2707641, 1995:543545, Dodey.

Chemical Abstracts Accession No. 106:95577 Romanenko et al., "Synthesis and Biological Activity of 3-Methyl, 7- or 8-alkyl-7,8dialkyl, heterocyclic, and cyclohexylaminoxanthines," Zaporozh. Med. Institute (1986).

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexyl-aminoxanthines," Zapoeozh, USSR, Farmatsevtichnii Zhurnal, 1986, (Kiev), vol. 5, 1986, pp. 41-44.

Clinical Trials. NCTO0622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.gov/ct2/show/.

Clinical Trials. "View of NCT00601250 on 1008-01-25: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCT00601250/2008__01__25 [retrieved on Feb. 27, 2009].

Clinical Trials. View of NCT00730275 on Aug. 7, 2008. "A study to assess the pharmacokinetics, safety and tolerability of Sitagliptin i adolescents".

Conarello, S.L. et al., "Mice lacking dipeptidyl peptidase IV are protected against obesity and insulin resistance". PNAS, May 27, 2003, vol. 100, No. 11, p. 6825-6830.

Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

Deacon, C.F., et al. Inhibitors of dipeptidyl peptidase IV: a novel approach for the prevention and treatment of Type 2 diabetes? Expert Opinion on Investigational Drugs, 2004, September, vol. 13, No. 9, p. 1091-1102.

DeMeester, I. et al.; "CD26, let it cut or cut it down", Review: Immunology Today; Aug. 1999, vol. 20, No. 8 pp. 367-375.

Dugi, K.A. et al., "BI 1356, a novel xanthine-based DPP-IV inhibitor, exhibits high potency with a wide therapeutic window and significantly reduces postprandial glucose excursions after an oGTT". Diabetologia, vol. 50, No. Suppl 1, Sep. 2007, p. S367, and 43rd Annual Meeting of the European Association for the Study of Diabetes; Amsterdam, Netherlands, Sep. 18-21, 2007.

Eckhardt Matthias et al: 8-(3-(R)-aminopiperidin-1-yl)-7-but-2-yny 1-3-methyl-1-(4-methyl-quina zolin-2-ylmethyl)-3,7-dihydropurine-2,6-dione (BI 1356), a highly potent, selective, long-acting, and orally bioavailable DPP-4 inhibitor for the treatment of

(56) References Cited

OTHER PUBLICATIONS type 2 diabetes: Journal of Medicinal Chemistry, American Chemical Society. Washington.; US, vol. 50, No. 26, Dec. 1, 2007, p. 6450-6453.

Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.

Elrishi M A et al: "The dipeptidyl-peptidase-4 (D::-4) inhibitors: A new class of oral therapy for patients with type 2 diabetes mellitus" Practical Diabetes International Chichester, vol. 24, No. 9, Nov. 1, 2007 pp. 474-482.

Gallwitz, B. et al., "Saxagliptin, a dipeptidyl peptidase IV inhibitor for the treatment of type 2 diabetes". IDRUGS, vol. 11, No. 12, Dec. 2008, p. 906-917.

Garber, A.J. et al., "Update: Vildaglitin for the treatment of Type 2 diabetes" Expert Opinion on Investigational Drugs, 200801GB, vol. 17, No. 1, Jan. 2008, p. 105-113.

Garcia-Soria, et al., "The dipeptidyl peptidase-4 inhibitor PHX1149 improves blood glucose control in patents with type 2 diabetes mellitus". Diabetes, Obesity and Metabolism, Apr. 2008, vol. 10, No. 4, p. 293-300.

Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.

Giron, D.; Thermal Analysis and Calorimetric Methods in the Characterisation of Polymorphs and Solvates; Thermochimica Acta (1995) vol. 248 pp. 1-59.

Graefe-Mody et al., "The novel DPP-4 inhibitor" Diabetes, (online) 2008, XP002561421 http://professional.diabetes.org/content/posters/2008/p553-p.pdf.

Greene, T.W, et al., "Protection for the Amino Group". Protective Groups in Organic Synthesis, 3rd edition, 1999, p. 494-653.

Gwaltney, S. "Medicinal Chemistry Approaches to the Inhibition of Dipeptidyl Peptidase IV", Current Topics in Medicinal Chemistry, 2008, 8, p. 1545-1552.

He, Y.L. et al., "The influence of hepatic impariment on the pharmacokinetics f the dipeptidyl peptidase IV (DPP-4) inhibitor vildagliptin" European Journal of Clinical Pharmacology, vol. 63, No. 7, May 8, 2007, p. 677-686.

Huettner Silks et al: "BI 1356, a novel and selective xanthine based DPP-IV inhibitor, demonstrates good safety and tolerability with a wide therapeutic window" Diabetes< American Diabetes Association, US, vol. 56, No. Suppl 1, Jun. 1, 2007, p. A156.

International Search Report for PCT/EP2007/054270 mailed Aug. 14, 2007.

JANUVIA; Patient Information; 2010.

Kanada, S. et al., "Safety, tolerability, pharmacokenetics and pharmacodynamics of multiple doses of BI 1356 (proposed tradename Ondero), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA , Jun. 6-10, 2008.

Kim, D. et al., "(2R)-4-Oxo-4-(3-(Trifluoremethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV inhibitor for the Treatment of Type 2 Diabetes." Journal Med. Chem, 2005, 48, p. 141-151.

Korom, S. et al; Inhibition of CD26/dipeptidyl peptidase IV activity in vivo prolongs cardiac allograft survival in rat recipients1 ,2, Transplantation, May 27, 1997, vol. 63, No. 10, pp. 1495-1500.

Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.

March, J. "Advanced Organic Chemistry: Reactions, Mechanisms, and Structure". Fourth Edition, 1992, pp. 652-653.

Mendes, F.D, et al. "Recent advances in the treatment of non-alcoholic fatty liver disease". Expert Opinion on Investigational Drugs, vol. 14, No. 1, Jan. 1, 2005, p. 29-35.

O'Farrell, et al., "Pharmacokinetic and Pharmacodynamic Assessments of the Dipeptidyl Peptidase-4 Inhibitor PHX1149: Double-Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.

Patani George A. et al.: "Bioisoterism : A Rational Approach in Drug Design", Chemical Reviews, 1996, vol. 96, No. 8, pp. 3147-3176.

TRADJENTA. Highlights of Prescribing Information (Revised Sep. 2012).

Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.

Pospisilik, et al; Dipeptidyl Peptidase IV Inhibitor Treatment Stimulates? -Cell Survival and Islet Neogenesis in Streptozotocin-Induced Diabetic Rats; Diabetes, vol. 52, Mar. 2003 pp. 741-750.

Priimenko, B. A., et al; Synthesis and Pharmacological Activity of Derivates of 6,8-Dimethyl Imidazo(1,2-f) Xanthine-(Russ.); Khimiko-Farmatsevticheskii zhurnal (1984) vol. 18, No. 12 pp. 1456-1461.

Rhee et al.: "Nitrogen-15-Labeled Deoxynucleosides. 3. Synthesis of [3-15N]-2'-Deoxyadenosine" J. Am. Chem. Soc. 1990, 112, 8174-8175.

Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.

Salomon, J., et al; Ultraviolet and g-Ray-Induced Reactions of Nucleic Acid Constituents. Reactions of Purines with Amines; Photochemistry and Photobiology (1974) vol. 19 pp. 21-27.

Schwartz, M. S. et al., "Type 2 Diabetes Mellitus in Childhood: Obesity and Insulin Resistance". JAOA Review Article, vol. 108, No. 9, Sep. 2008, p. 518.

Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Stahl, P.H., "Handbook of Pharmaceutical Salts". C.G. Wermuth, Wiley-VCH, 2002, p. 61.

Tamm, E, et al., "Double-blind study comparing the immunogenicity of a licensed DTwPHib-CRM197 conjugate vaccine (Quattvaxem TM) with three investigational, liquid formulations using lower doses of Hib-CRM197 conjugate". Science Direct, Vaccine, Feb. 2005, vol. 23, No. 14, p. 1715-1719.

Tanaka, S., et al; "Suppression of Arthritis by the Inhibitors of Dipeptidyl Peptidase IV," In. J. Immunopharmac., vol. 19, No. 1, pp. 15-24, 1997.

Thomas, Leo et al: "(R)-8-(3-Amino-piperidin-1-yl)-7-but-2-ynyl-3-methyl-1- (4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics, American Socity for Therapeutics, US, vol. 325, No. 1, Apr. 1, 2008, pp. 175-182 abstract p. 177, col. 2, paragraph 1 table 1 p. 1B1, col. 2, last paragraph—p. 182, col. 1.

U.S. Appl. No. 12/724,653, filed Mar. 16, 2010—Xanthine Derivatives, the Preparation Thereof and Their Use as Pharmaceutical Compositions. Inventor: Frank Himmelsbach, et al.

U.S. Appl. No. 12/767,855, filed Apr. 27, 2010—Xanthine Derivatives, the Preparation Thereof and Their use as Pharmaceutical Compositions. Inventor: Frank Himmelsbach, et al.

Villhauer, E.B., "1-[[3-Hydroxy-1-adamantyl)amino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.

Villhauer, E.B., et al., "1-{2-{5-Cyanopyridin-2-yl)amino}-ethylamino}acetyl-1-1(S)-pyrrolidine-carbonitrile: A Potent, Selec-

(56) References Cited

OTHER PUBLICATIONS tive, and Orally Bioavailable Dipeptidyl Peptidase IV Inhibitor with Antihyperglycemic Properties". Journal of Medical Chemistry, 2002, vol. 45, No. 12, p. 2362-2365.
Wang Y et al: "BI-1356. Dipeptidyl-peptidase IV inhibitor, antidiabetic agent" Drugs of the Future, Prous Science, ES, vol. 33, No. 6, 1 June 208, pp. 473-477, Jun. 1, 2008.
White, J.R., "Dipeptidyl Peptidase-IV Inhibitors: Phamacological Profile and Clinical Use". Clinical Diabetes, vol. 26, 2008, p. 53-57.
Wikipedia, Annulation. Jun. 23, 2008, http://en.wikipedia.org/wiki/Annelation.
Wolff, M.E.: "Burger's Medicinal Chemistry and Drug Discovery" Fifth Edition, vol. 1: Principles and Practice, pp. 975-977, 1994, John Wiley & Sons, Inc.
World Health Organization (WHO). "Addendum 1 to "The use of stems in the selection of International Nonproprietary names (INN) for pharmaceutical substances"" Online Jun. 19, 2007, pp. 1-3, retrieved from URL: http://www.who.int/medicindedocs/index/assoc/s1414e/s1414e.pdf.
Yasuda, et al. "E3024 3-but-2-ynyl-5-methyl-2-piperazin-1-yl-3,5-dihydro-4H-imidazol [ 4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.
Yoshikawa, Seiji et al.: Chemical Abstract of Japanese Patent No. WO 2003/104229 Preparation of purinone derivatives as dipeptidylpeptidase IV (DPP-IV) inhibitors, 2003.
Zejc, Alfred, et al; "Badania Nad Piperazynowymi Pochodnymi Dwumetyloksantyn" Acta Polon Pharm, XXXV (1976) Nr. 4 pp. 417-421.
Zhong, Qing et al; "Glucose-dependent insulinotropic peptide stimulates proliferation and TGF-? release from MG-63 cells," Peptides 24 (2003) 611-616.
Zimmer et al; Synthesis of 8-Substituted Xanthines and their Oxidative Skeleton Rearrangement to 1-Oxo-2,4,7,9-tetraazaspiro[4,5]dec-2-ene-6,8,10-triones; Euripean Journal Organic Chemistry (1999) vol. 9 pp. 2419-2428.
Dave, K.G. et al., "Reaction of Nitriles under Acidic Conditions, Part I. A General Method of Synthesis of Condensed Pyrimidines", J. Heterocyclic Chemistry, BD, 17, 1, ISSN 0022-152X,Nov. 1980, p. 1497-1500.
Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.
International Search Report and Written Opinion for PCT/EP2010068349 mailed Feb. 4, 2011.
Florez, Jose C., et al., "TCF7L2 Polymorphisms and progression to diabetes in the diabetes prevention program". New England Journal of Medicine, MA Medical Society, vol. 355, No. 2, Jul. 20, 2006, p. 241-250.
Sathananthan, A., et al., "Personalized pharmacotherapy for type 2 diabetes mellitus". Personalized Medicine 2009 Future Medicine Ltd, vol. 6, No. 4, Jul. 2009, p. 417-422.
Clinical Trials: NCT00622284. Efficacy and Safety of BI 1356 in Combination with Metformin in Patients with Type 2 Diabetes. Boehringer Ingelheim Pharmaceuticals, Aug. 2008.
Clinical Trials: NCT00602472. "BI 1356 in combination withe metformin and a sulphonylurea in Type 2 Diabetes". DrugLib.com, Nov. 3, 2008.
Clinical Trials: NCT00798161. "Safety and efficacy of Bi 1356 Plus Metformin in Type 2 Diabetes, Factorial Design". Clinical Trials.gov archive. A Service of the U.S> National Institutes of Health. Nov. 24, 2008, p. 1-3.
Merck: "Initial Therapy with Janumet (sitagliptin/metformin) provided significantly greater blood sugar lowering compared to metformin alone in patients with type 2 diabetes". Webwire.com, Jun. 8, 2009, p. 1-4.
Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.
Thomas, L, et al: "BI 1356, a novel and selective xanthine beased DPP-IV inhibitor, exhibits a superior profile when compared to sitagliptin and vildagliptin." Diabetologoa, vol. 50, No. Suppl. 1, Sep. 2007, p. S363.
Ahren B: "DPP-4 inhibitors", Best practice and research in clinical endocrinology and metabolism—New therapies for diabetes 200712 GB LNKD- DOI:10.1016/J. Beem.2007.07.005, vol. 21, No. 4, Dec. 2007, pp. 517-533.
International Search Report for PCT/EP2010/064691 mailed Jan. 20, 2011.
International Search Report and Written Opinion for PCT/EP2009/061659 mailed Mar. 9, 2010.
International Search Report and Written Opinion for PCT/EP2009/063511 mailed Feb. 26, 2010.
International Search Report for PCT/EP2010/051093 mailed Jul. 14, 2010.
Bundgaard, H. "Design of prodrugs: Bioreversible derivatives for various functional groups and chemical entities". Royal Danish School of Pharmacy, 1985, p. 1-92.
Sauer, R, et al. "Water-soluble phosphate prodrugs of 1-Propargyl-7-styrylxanthine derivatives, A2A-selective adenosine receptor antagonists". Journal Med. Chem., vol. 43, Issue 3, Jan. 2000, p. 440-448.
Shintani, Maki, et al., "Insulin Resistance and Genes" Circulatory Sciences (1997) vol. 17, No. 12 pp. 1186-1188.
Targher, G. et al., "Prevalence of Nonalcoholic Fatty Liver Disease and Its Association With Cardiovascular Disease Among Type 2 Diabetic Patients." Diabetes Care, 2007, vol. 30, No. 5, pp. 1212-1218.
Tounyoubyou, "Symposium-19: Future Perspectives on Incretion Therapy in Diabetes." 2008, vol. 51, Suppl. 1, p. S-71, S19-2.
Tradjenta, Highlights of Prescribing Information (revised Sep. 2012).
Tribulova, N. et al. "Chronic Disturbances in NO Production Results in Histochemical and Subcellular Alterations of the Rat Heart." Physiol. Res., 2000, vol. 49, No. 1, pp. 77-88.
Ahren, Bo, et al; Improved Meal-Related b-Cell Function and Insulin Sensitivity by the Dipeptidyl Peptidase-IV Inhibitor Vildagliptin in Metformin-Treated Patients with Type 2 Diabetes Over 1 Year; Diabetes Care (2005) vol. 28, No. 8 pp. 1936-1940.
Anstee, Quentin M. et al. "Mouse models in non-alcoholic fatty liver disease and steatohepatitis research" (2006) International Journal of Expermental Pathology, vol. 87, pp. 1-16.
Berge, S. et al., "Pharmaceutical Salts." Journal of Pharmaceutical Sciences, 1977, vol. 66, No. 1, pp. 1-19.
Bosi, E. et al., "Effects of Vildagliptin on Glucose Control Over 24 Weeks in Patients With Type 2 Diabetes Inadequately Controlled With Metformin." Diabetes Care, 2007, vol. 30, No. 4, pp. 890-895.
Brazg, Ronald, et al; Effect of Adding MK-0431 to On-Going Metforming Therapy in Type 2 Diabetic Patients Who Have Inadequate Glycemic Control on Metformin; Diabetes ADA (2005) vol. 54, Suppl. 1 p. A3.
Charbonnel, B. et al., "Efficacy and Safety of the Dipeptidyl Peptidase-4 Inhibitor Sitagliptin Added to Ongoing Metformin Therapy in Patients With Type 2 Diabetes Inadequately Controlled With Metformin Alone." Diabetes Care, 2006, vol. 29, No. 12, pp. 2638-2643.
Charkevich, D. A., Pharmacology, M., Medicina, 1987, pp. 47-48.
Clinical Trial NCT00622284 (published online at clinicaltrials.gov on Feb. 22, 2008).
Deacon, Carolyn F. et al. "Linaglipitn, a xanthine-based dipeptidyl peptidase-4 inhibitor with an unusual profile for the treatment of type 2 diabetes" Expert Opin. Investig. Drugs (2010) 19(1): 133-140.
Definition of "prevent", e-dictionary, Aug. 15, 2013, http://dictionary.reference.com/browse/prevent.
Drucker, et al.., The incretin system:glucagon-like peptide-1 receptor agonists and dipeptidyl peptidase-4 inhibitors in type 2 diabetes. Lancet, 2006, 368: 1696-705.
Edosada, C. Y. et al. "Selective Inhibition of Fibroblast Activation Protein Protease Based on Dipeptide Substrate Specificity." The Journal of Biological Chemistry, 2006, vol. 281, No. 11, pp. 7437-7444.

(56) References Cited

OTHER PUBLICATIONS

Ferreira, L. et al., "Effects of Sitagliptin Treatment on Dysmetabolism, Inflammation, and Oxidative Stress in an Animal Model of Type 2 Diabetes (ZDF Rat)." Mediators of Inflammation, 2010, vol. 2010, pp. 1-11.
Florez, J. et al. "TCF7L2 Polymorphisms and Progression to Diabetes in the Diabetes Prevention Program." The New England Journal of Medicine, 2006, vol. 355, No. 3, pp. 241-250.
Gallwitz, B. et al., DPP IV inhibitors for the Treatment of Type 2 Diabetes; Diabetes Frontier (2007) vol. 18, No. 6 pp. 636-642.
Garber, A. J. et al., "Effects of Vildagliptin on Glucose Control in Patients with Type 2 Diabetes Inadequately Controlled with a Sulphonylurea". Diabetes, Obesity and Metabolism (2008) vol. 10 pp. 1047-1055.
Hayashi, M. "Recipe for Oral Hypoglcemic Agents According to Pathological Condition." Pharmacy, 2006, vol. 57, No. 9, pp. 2735-2739.
Hayashi, Michio., "Recipe for Oral Hypoglycemic Agents to Pathological Condition" Pharmacy (2006) vol. 57, No. 9 pp. 2735-2739.
Herman, Gary et al. "Co-Administration of MK-0431 and Metformin in Patients with Type 2 Diabetes Does Not Alter the Pharmacokinetics of MK-0431 or Metformin" (2005) Journal of American Diabetes Association vol. 54, Supplement 1, 3 pgs.
Hermann, Robert, et al; Lack of Association of PAX4 Gene with Type 1 Diabetes in the Hungarian Populations; Diabetes (2005) vol. 54 pp. 2816-2819.
Hermansen, K., "Efficacy and Safety of the Dipeptidyl Peptidase-4 Inhibitor, Sitagliptin, in Patients with Type 2 Diabetes Mellitus Inadequately Controlled on Glimepiride Alone or on Glimepiride and Metformin". Diabetes, Obesity and Metabolism (2007) vol. 9, No. 5 pp. 733-745.
Hu, Y. et al., "Synthesis and Structure-activity Relationship of N-alkyl Gly-boro-Pro Inhibitors of DPP4, FAP, and DPP7." Bioorganic & Medicinal Chemistry Letters 15, 2005, pp. 4239-4242.
Huttner, S. et al., "Safety, Tolerability, Pharmacokinetics, and Pharmacodynamics of Single Oral Doses of BI 1356, an Inhibitor of Dipeptidyl Peptidase 4, in Healthy Male Volunteers." Journal of Clinical Pharmacology, 2008, vol. 48, No. 10, pp. 1171-1178.
International Search Report and Written Opinion for PCT/EP2011/057256 mailed Jul. 22, 2011.
Inukai, T., "Treatment of Diabetes in Patients for Whom Metformin Treatment is Not Appropriate." Modern Physician, 2008, vol. 28, No. 2, pp. 163-165.
Kharkevich, D. A., "Educational Literature" Pharmacology (1987) Third Edition, Meditsina Press, Moscow pp. 47-48.
Kibbe, Editor. Handbook of Pharmaceuticals Excipiets, Third Edition, Copovidon-pp. 196-197, Date of Revision: Dec. 16, 2008. Mannitol-pp. 424-425, Date of Revision: Feb. 19, 2009.
Kim, Kwang-Rok et al. "KR-62436, 6-{2-[2-(5-cyano-4,5-dihydropyrazol-1-yl)-2-oxoethylamino]ethylamino}nicotinonitrile, is a novel dipeptidyl peptidase-IV (DPP-IV) inhibitor with anti-hyperglycemic activity" European Journal of Pharmacology 518 (2005) pp. 63-70.
Komori, Kiyoshi., "Treatment of Diabetes in Patients for Whom Metforming Treatment is Not Appropriate" Modern Physician (2008) vol. 27, No. 2 pp. 163-165.
Lakatos, P. L. et al., "Elevated Serum Dipeptidyl IV (CD26, EC 3.4.14.5) Activity in Experimental Liver Cirrhosis." European Journal of Clinical Investigation, 2000, vol. 30, No. 9, pp. 793-797.
Matsumiya, T. et al., "Therapeutic Drugs for Clinicians." Diagnosis and Therapy, 2008, vol. 96, No. 2, pp. 389-390.
Matsumiya, Teruhiko, et al., "Therapeutic Drugs for Clinicians" Diagnosis and Treatment (2008) vol. 96, No. 2 pp. 389-390.
Mayo Clinic Staff: "Nonalcohoholic fatty liver disease: Prevention" [retrieved on Nov. 30, 2012]. retrieved from the Internet: ,URL: http://www.mayoclinic.com/health/nonalcoholic-fatty-liver-disease/DS00577DSECTION=prevention>.
Nauck, M. A. et al., "Efficacy and Safety of Adding the Dipeptidyl Peptidase-4 Inhibitor Alogliptin to Metformin Therapy in Patients with Type 2 Diabetes Inadequately Controlled with Metformin Monotherapy: A Multicentre, Randomised, Double-Blind, Placebo-Cotrolled Study." Clinical Practice, 2008, vol. 63, No. 1, pp. 46-55.
Nauck, M. A. et al., "Efficacy and Safety of the Dipeptidyl Peptidase-4 Inhibitor, Sitagliptin, Compared with the Sulfonylurea, Glipizide, in Patients with Type 2 Diabetes Inaduately Controlled on Metformin alone: A Randomized, Double-Blind, Non-Inferiority Trial." DIabetes Obesity and Metabolism, 2007, vol. 9, No. 2, pp. 194-205.
Nihon Ijinpo, Japan Medicinal Journal, 2001, No. 4032, p. 137.
Office Action for U.S. Appl. No. 10/695,597 mailed May 2, 2008.
Plummer, C.J.G. et al., "The Effect of Melting Point Distributions on DSC Melting Peaks." Polymer Bulletin, 1996, vol. 36, pp. 355-360.
Sarafidis, Panteleimon et al. "Cardiometabolic Syndrome and Chronic Kidney Disease: What is the Link?" JCMS (2006) 1: pp. 58-65.
Schmidt, D. et al., "Fibromatosis of Infancy and Childhood Histology, Ultrastructure and Clinicopathologic Correlation." Zeitschrift für Kinderchirurgie, 1985, vol. 40, No. 1, pp. 40-46.
Shanks, N. et al., Are animal models predictive for humans?, PEHM, Philosophy, Ethics, and Humanaities in Medicine, 4(2), 2009, 1-20.
Shintani, M. et al. "Insulin Resistance and Genes." Circulatory Science, 1997, vol. 17, No. 12, pp. 1186-1188.
Augusti, D.V. et al., "Quantitative determinatio of the enantiomeric composition of thalidomide solutions by electrospray ionizatio tandem mass spectrometry". Chem Comm, 2002, p. 2242-2243.
Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.
International Search Report and Written Opinion for PCT/EP2007/054270 mailed Aug. 14, 2007.
International Search Report and Written Opinion for PCT/EP2011/054169 mailed Aug. 4, 2011.
International Search Report and Written Opinion for PCT/EP2011/057163 mailed Jun. 27, 2011.
Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.
X-Ray Diffraction. The United States Pharmacopeia, 2002, USP 25 NF20, p. 2088-2089.
Abstract in English for German DE10109021, 2002.
Anstee, Quentin M., "Mouse models in non-alcoholic fatty liver disease and steatohepatitis research" (2006) International Journal of Experimental Pathology, v. 87, p. 1-16.
Chemistry Review: Tradjenta, "NDA 201280, CMC Director Review Tradjenta (Linagliptin) Tablets." Center for Drug Evaluation and Research, Aug. 9, 2010, Retrieved from the internet on Nov. 1, 2013, http://www.accessdata.fda.gov/drugsatfda_docs/nda/2011/201280Orig1s000ChemR.pdf.
Dave, Rutesh H. "Overview of pharmaceutical excipients used in tablets and capsules." Drug Topics, Oct. 24, 2008.
Diabetesincontrol.com "EASD: Eucreas, a Combination of Galvus and Metformin, Recommended for Approval." Diabetes In Control.com, Sep. 25, 2007, Retrieved from internet on Nov. 30, 2012, http://www.diabetesincontrol.com/articles/53-diabetes-news/5145.
Ferry, Robert Jr., "Diabetes Causes." eMedicine Health, MedicineNet.com, 2013, Retrieved from internet on Aug. 22, 2013, http://www.onhealth.com/diabetes_health/page3.htm#diabetes_causes.
Gennaro, Alfonso R. Remington Farmacia, 2003, Spanish copy: p. 828, English copy: pp. 711-712, Preformulation, Chapter 38.
Halimi, et al., "Combination treatment in the management of type 2 diabetes focus on vildagliptin and metformin as a single tablet", Vascualr Health and Risk Management, 2008, 4(3) p. 481-92.
Horsford, E. N. "On the source of free hydrochloric acid in the gastric juice." Proceedings of the Royal Society of London, Published in 1868-1869, vol. 17, pp. 391-395.
Kibbe, A., Editor. Handbook of Pharmaceutical Excipients, Third Edition, Copovidon-pp. 196-197, Date of Revision: Dec. 16, 2008. Mannitol-pp. 424-425, Date of Revision: Feb. 19, 2009, Published in 2009.

(56) References Cited

OTHER PUBLICATIONS

Kim, Kwang-Rok et al., "KR-62436, 6-{2-{2-(5-cyano4,5-dihydropyrazol-1-yl)-2-oxoethylamino}ethylamino} nicotinonitrile, is a novel dipeptidyl peptidase-IV (DDP-IV inhibitor with anti-hyperglycemic activity" European Journal of Pharmacology 518, 2005, p. 63-70.

Lakatos, P. L., et al., "Elevated Serum Dipeptidyl IV (CD26, EC3.4.14.5) Activity in Experimental Liver Cirrhosis" European Journal of Clinical Investigation, 2000, V. 30, No. 9, p. 793-797.

Medline Plus, "Obesity" 2013, Retrieved from internet on Aug. 22, 2013, http://www.nlm.nih.gov/medlineplus/obesity.html.

Nielsen, L., "Incretin mimetics and DPP-IV inhibitors for the treatment of type 2 diabetes." Drug Discovery Today, 2005, vol. 10, No. 10, pp. 703-710.

Russell-Jones, D. et al., "Liraglutide vs insulin glargine and placebo in combination with metformin and sulfonylurea therapy in type 2 diabetes mellitus (LEAD-5 met+SU): a randomised controlled trial." Diabetologia, 2009, vol. 52, pp. 2046-2055.

Sarafidis, P. et al., "Cardiometabolic Syndrome and Chronic Kidney Disease: What is the link?"JCMS 2006, 1: p. 58-65.

St. John Providence Health Center, "Preventing Obesity in Children and Teens." Retrieved from internet on Aug. 22, 2013, http://www.stjohnprovidence.org/Health_InfoLib/swarticle.aspx?type=85&id=P07863.

Sune Negre, J. M. "New Galenic Contributions to Administration Forms". Continued Training for Hospital Pharmacists 3.2., (Publication date unavailable), Retrieved from internet on Feb. 23, 2011, http://www.ub.es/legmh/capitols/sunyenegre.pdf.

United Healthcare, "Diabetes." Retrieved from internet on Aug. 22, 2013, http://www.uhc.com/source4women/health_topics/diabetesirelatedinformation/dOf0417b073bf11OVgnVCM1000002f1Ob1Oa_htm.

\* cited by examiner

USES OF DPP-IV INHIBITORS

This application claims priority of EP 06 009 203, which is hereby incorporated by reference in its entirety.

BACKGROUND OF THE INVENTION

1. Field of the Invention

The specification describes the use of selected DPP IV inhibitors for the treatment of physiological functional disorders and for reducing the risk of the occurrence of such functional disorders in at-risk patient groups. In addition, the use of the above-mentioned DPP IV inhibitors in conjunction with other active substances is described, by means of which improved treatment outcomes can be achieved. These applications may be used to prepare corresponding medicaments.

2. Description of the Prior Art

The enzyme DPP-IV, also known by the name CD26, is a serine protease which promotes the cleaving of dipeptides in proteins with a proline or alanine group at the N-terminal end. DPP-IV inhibitors thereby influence the plasma level of bioactive peptides including the peptide GLP-1 and are highly promising molecules for the treatment of diabetes mellitus.

Type 1 diabetes mellitus, which occurs mainly in juveniles under 30 years of age, is categorised as an autoimmune disease. With a corresponding genetic disposition and under the influence of various factors, insulitis occurs, followed by destruction of the B-cells, so that the pancreas is no longer able to produce much, if any, insulin.

Type 2 diabetes mellitus is not categorised as an autoimmune disease and manifests itself in a fasting blood sugar level exceeding 125 mg of glucose per dl of plasma; the measurement of blood glucose values is a standard procedure in routine medical analysis. Prediabetes is suspected if the fasting blood sugar level exceeds the maximum normal level of 99 mg of glucose per dl of plasma but does not exceed the threshold of 125 mg of glucose per dl of plasma, which is relevant for diabetes. This is also referred to as pathological fasting glucose (impaired fasting glucose). Another indication of prediabetes is a disrupted glucose tolerance, i.e. a blood sugar level of 140-199 mg of glucose per dl of plasma 2 hours after taking 75 mg of glucose on an empty stomach within the scope of an oral glucose tolerance test.

If a glucose tolerance test is carried out, the blood sugar level of a diabetic will be in excess of 199 mg of glucose per dl of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject the blood sugar level will be between 60 and 99 mg per dl of plasma before taking the glucose, less than 200 mg per dl 1 hour after taking it and less than 140 mg per dl after 2 hours. If after 2 hours the value is between 140 and 199 mg this is regarded as abnormal glucose tolerance or in some cases glucose intolerance.

In the monitoring of the treatment of diabetes mellitus the HbA1c value, the product of a non-enzymatic glycation of the haemoglobin B chain, is of exceptional importance. As its formation depends essentially on the blood sugar level and the life time of the erythrocytes the HbA1c in the sense of a "blood sugar memory" reflects the average blood sugar level of the preceding 4-12 weeks. Diabetic patients whose HbA1c level has been well controlled over a long time by more intensive diabetes treatment (i.e. <6.5% of the total haemoglobin in the sample) are significantly better protected from diabetic microangiopathy. The available treatments for diabetes can give the diabetic an average improvement in their HbA1c level of the order of 1.0-1.5%. This reduction in the HbA1C level is not sufficient in all diabetics to bring them into the desired target range of <6.5% and preferably <6% HbA1c.

If insulin resistance can be detected this is a particularly strong indication of the presence of the complex metabolic disorder of prediabetes. Thus, it may be that in order to maintain glucose homoeostasis a person needs 2-3 times as much insulin as another person. The most certain method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. Another method of measurement is the mathematical HOMA model. The insulin resistance is calculated by means of the fasting plasma glucose and the fasting insulin concentration. In this method it is not possible to distinguish between hepatic and peripheral insulin resistance. These processes are not really suitable for evaluating insulin resistance in daily practice. As a rule, other parameters are used in everyday clinical practice to assess insulin resistance. Preferably, the patient's triglyceride concentration is used, for example, as increased triglyceride levels correlate significantly with the presence of insulin resistance.

To simply somewhat, in practice it is assumed that people are insulin-resistant if they have at least 2 of the following characteristics:
1) overweight or obesity
2) high blood pressure
3) dyslipidaemia (an altered content of total lipids in the blood)
4) at least one close relative in whom abnormal glucose tolerance or type 2 diabetes has been diagnosed.

Overweight means in this instance that the Body Mass Index (BMI) is between 25 and 30 kg/m$^2$, the BMI being the quotient of the body weight in kg and the square of the height in meters. In manifest obesity the BMI is 30 kg/m$^2$ or more.

It is immediately apparent, from the above definition of insulin resistance, that hypotensive agents are suitable and indicated for treating it if, among other things, high blood pressure is found in the patient.

A similar indication of prediabetes is if the conditions for metabolic syndrome are met, the main feature of which is insulin resistance. According to the ATP IHINCEP Guidelines (Executive Summary of the Third Report of the National Cholesterol Education Program (NCEP) in the Journal of the American Medical Association 285:2486-2497, 2001) metabolic syndrome is present if a patient has at least 3 of the following characteristics:
1) Abdominal obesity, defined as a waist measurement of >40 inches or 102 cm in men and >35 inches or 94 cm in women
2) Triglyceride levels>150 mg/dl
3) HDL-cholesterol levels<40 mg/dl in men
4) High blood pressure>130/>85 mm Hg
5) Fasting blood sugar of >110 mg/dl This definition of metabolic syndrome immediately shows that hypotensives are suitable for treating it if the patient is found to have high blood pressure, among other things.

A triglyceride blood level of more than 150 mg/dl also indicates the presence of pre-diabetes. This suspicion is confirmed by a low blood level for HDL cholesterol. In women, levels below 55 mg per dl of plasma are regarded as too low while in men levels below 45 mg per dl of plasma are regarded as too low. Triglycerides and HDL cholesterol in the blood can also be determined by standard methods in medical analysis and are described for example in Thomas L (Editor): "Labor and Diagnose", TH-Books Verlagsgesellschaft mbH, Frankfurt/Main, 2000. A suspicion of prediabetes is further confirmed if the fasting blood sugar levels also exceed 99 mg of glucose per dl of plasma.

The term gestational diabetes (diabetes of pregnancy) denotes a form of the sugar disease which develops during pregnancy and usually ceases again immediately after the birth. Gestational diabetes is diagnosed by a screening test which is carried out between the 24th and 28th weeks of pregnancy. It is usually a simple test in which the blood sugar level is measured one hour after the administration of 50 g of glucose solution. If this 1 h level is above 140 mg/dl, gestational diabetes is suspected. Final confirmation may be obtained by a standard glucose tolerance test with 75 g of glucose.

Hyperglycaemia describes a functional disorder in which an excessively high glucose level is measured in the blood, either in the fasting state (increased glucose level of 100-125 mg/dl or diabetic-hyperglycaemic level of >125 mg/dl compared with the normal level of <100 mg/dl,) or in non-fasting state (elevated glucose level of >180 mg/dl).

By adrenergic postprandial syndrome (reactive hypoglycaemia) the clinician means a functional disorder in which a disproportionately high insulin level leads to a drop in the blood sugar level (hypoglycaemia) caused by an imbalance between rapidly digested carbohydrates and a high insulin level persisting after a meal.

The term diabetic foot refers to lesions on the foot caused by diabetes mellitus, the primary cause of which is a polyneuropathy that can be put down to inadequate metabolic control. A diabetic foot is diagnosed by the occurrence of typical lesions (e.g. ulcers) in an existing case of diabetes mellitus.

The term diabetes-associated ulcer refers to an ulcerous inflammatory skin defect in a patient with diabetes mellitus. A diabetes-associated ulcer is diagnosed by typical anamnesis and physical examination (e.g. inspection of the foot).

The term diabetic hyperlipidaemia is used if a patient with diabetes mellitus suffers an increase in total cholesterol or, more typically in diabetic hyperlipidaemia, an increase in the plasma triglycerides, with or without a reduction in HDL cholesterol.

The term diabetic dyslipidaemia is used if the total cholesterol is not raised but the distribution of HDL- and LDL-cholesterol is altered, i.e. the patient's HDL cholesterol level is too low (e.g. <55 mg/dl for women and <45 mg/dl for men).

The term heart failure is used if either subjective symptoms or objective findings indicate an inability of the heart to achieve the necessary ejection output. Subjective symptoms may be e.g. difficulty breathing under stress or at rest. Objective findings include a reduced ejection output of the heart according to ultrasound (reduced ejection volume), congestion of the lungs according to X-ray, and/or reduced walking distances.

DETAILED DESCRIPTION OF THE INVENTION

Some selected DPP IV inhibitors are particularly suitable for the preparation of a medicament for the therapeutic treatment of patients who have been diagnosed with a medical or physiological functional disorder selected from among prediabetes, glucose intolerance (impaired glucose tolerance), pathological fasting glucose (impaired fasting glucose), diabetic foot, diabetes-associated ulcer, diabetic hyperlipidaemia, diabetic dyslipidaemia, newly diagnosed type 1 diabetes (to maintain a residual secretion of insulin from the pancreas), gestational diabetes (diabetes of pregnancy), hyperglycaemia, adrenergic postprandial syndrome (reactive hypoglycaemia) or heart failure.

These medicaments may also be used to reduce the risk that in spite of treatment the patient will suffer an impaired glucose metabolism, an elevated HbA1c value, an impaired fasting glucose value, manifest type 2 diabetes, a diabetic foot, a diabetes-associated ulcer, diabetic hyperlipidaemia or diabetic dyslipidaemia, and that in spite of the therapy insulin treatment will become necessary or macrovascular complications will occur.

Examples of macrovascular complications of this kind are myocardial infarct, acute coronary syndrome, unstable angina pectoris, stable angina pectoris, haemorrhagic or ischaemic stroke, peripheral arterial occlusive disease, cardiomyopathy, left heart insufficiency, right heart insufficiency, global heart insufficiency, heart rhythm disorders and vascular restenosis. These macrovascular complications are known to the skilled man and described in detail in the standard textbooks.

In addition the substances are suitable for enhancing the vitality and secretion capacity of cells after the transplanting of islets of Langerhans or beta cells, and thereby ensuring a favourable outcome after transplantation. The substances may also be used during the isolation and transplantation phase of islets of Langerhans or beta cells, by adding the specified substances to the conventional isolation or storage medium in a suitable concentration of 1 nmol/l to 1 μmol/l, preferably in a concentration of 1 nmol/l to 100 nmol/l. This results in an improvement in the quality of the material to be transplanted. An improvement in quality is obtained particularly in combination with added amounts of GLP-1 (glucagon like peptide 1), preferably in a concentration of 1-100 nmol/l. Corresponding isolation or storage media and corresponding methods of enhancing the vitality and secretion capacity of islets of Langerhans or beta cells by the addition of DPP IV inhibitors to the media used are a further object of the invention.

Finally, the above-mentioned inhibitors are suitable for the treatment of various forms of arthritis, but particularly rheumatoid arthritis.

DPP IV inhibitors selected according to the present invention can be described by formula (I)

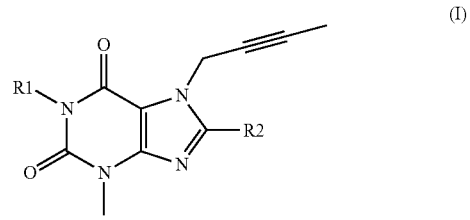

or formula (II)

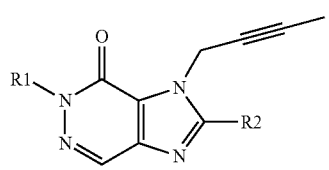

wherein R1 denotes ([1,5]naphthyridin-2-yl)methyl, (quinazolin-2-yl)methyl, (quinoxalin-6-yl)methyl, (4-methyl-quinazolin-2-yl)methyl, 2-cyano-benzyl, (3-cyano-quinolin-2-yl)methyl, (3-cyano-pyridin-2-yl)methyl, (4-methyl-pyrimidin-2-yl)methyl, or (4,6-dimethyl-pyrimidin-2-yl)methyl and R2 denotes 3-(R)-amino-piperidin-1-yl, (2-amino-2-methyl-propyl)-methylamino or (2-(S)-amino-propyl)-methylamino.

Particularly preferred DPP IV inhibitors are the following compounds and the therapeutically active salts thereof:
1-[(4-methyl-quinazolin-2-yl)methyl]-3-methyl-7-(2-butyn-1-yl)-8-(3-(R)-amino-piperidin-1-yl)-xanthine (cf. WO 2004/018468, Example 2 (142):

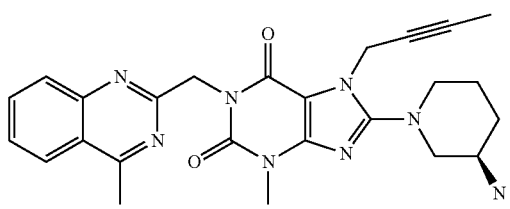 [SMILES: CC#CCn1c(N2CCC[C@@H](N)C2)nc2c1c(=O)n(Cc1nc(C)c3ccccc3n1)c(=O)n2C]

1-[([1,5]naphthyridin-2-yl)methyl]-3-methyl-7-(2-butyn-1-yl)-8-((R)-3-amino-piperidin-1-yl)-xanthine (cf. WO 2004/018468, Example 2 (252)):

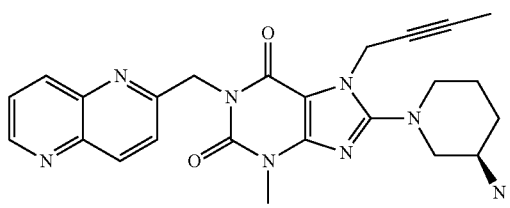 [SMILES: CC#CCn1c(N2CCC[C@@H](N)C2)nc2c1c(=O)n(Cc1ccc3ncccc3n1)c(=O)n2C]

1-[(quinazolin-2-yl)methyl]-3-methyl-7-(2-butyn-1-yl)-8-((R)-3-amino-piperidin-1-yl)-xanthine (cf. WO 2004/018468, Example 2 (80)):

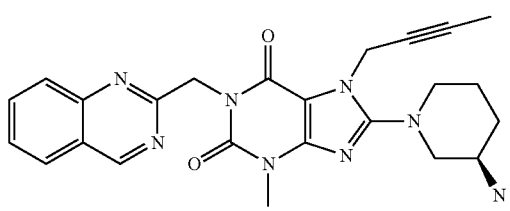 [SMILES: CC#CCn1c(N2CCC[C@@H](N)C2)nc2c1c(=O)n(Cc1ncc3ccccc3n1)c(=O)n2C]

2-((R)-3-amino-piperidin-1-yl)-3-(but-2-ynyl)-5-(4-methyl-quinazolin-2-ylmethyl)-3,5-dihydro-imidazo[4,5-d]pyridazin-4-on (cf. WO 2004/050658, Example 136):

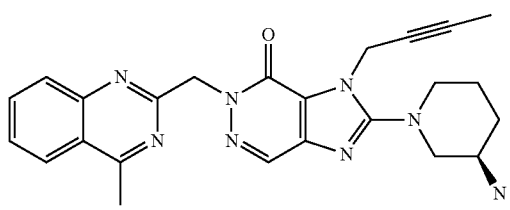 [SMILES: CC#CCn1c(N2CCC[C@@H](N)C2)nc2cnn(Cc3nc(C)c4ccccc4n3)c(=O)c21]

1-[(4-methyl-quinazolin-2-yl)methyl]-3-methyl-7-(2-butyn-1-yl)-8-[(2-amino-2-methyl-propyl)-methylamino]-xanthine (cf. WO 2006/029769, Example 2 (1)):

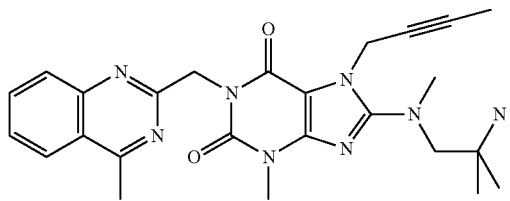 [SMILES: CC#CCn1c(N(C)CC(C)(C)N)nc2c1c(=O)n(Cc1nc(C)c3ccccc3n1)c(=O)n2C]

1-[(3-cyano-quinolin-2-yl)methyl]-3-methyl-7-(2-butyn-1-yl)-8-((R)-3-amino-piperidin-1-yl)-xanthine (cf. WO 2005/085246, Example 1 (30)):

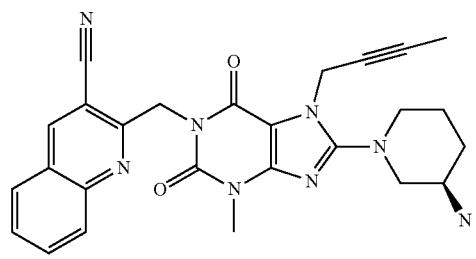 [SMILES: CC#CCn1c(N2CCC[C@@H](N)C2)nc2c1c(=O)n(Cc1nc3ccccc3cc1C#N)c(=O)n2C]

1-(2-cyano-benzyl)-3-methyl-7-(2-butyn-1-yl)-8-((R)-3-amino-piperidin-1-yl)-xanthine (cf. WO 2005/085246, Example 1 (39)):

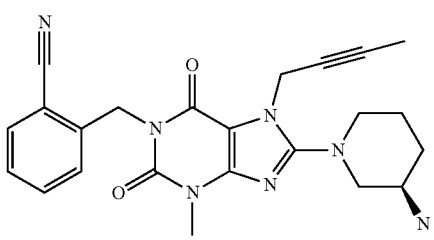 [SMILES: CC#CCn1c(N2CCC[C@@H](N)C2)nc2c1c(=O)n(Cc1ccccc1C#N)c(=O)n2C]

1-[(4-methyl-quinazolin-2-yl)methyl]-3-methyl-7-(2-butyn-1-yl)-8-[(S)-(2-amino-propyl)-methylamino]-xanthine (cf. WO 2006/029769, Example 2 (4)):

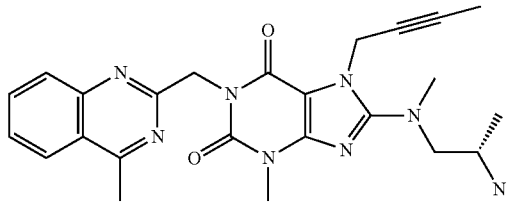 [SMILES: CC#CCn1c(N(C)C[C@H](C)N)nc2c1c(=O)n(Cc1nc(C)c3ccccc3n1)c(=O)n2C]

1-[(3-cyano-pyridin-2-yl)methyl]-3-methyl-7-(2-butyn-1-yl)-8-((R)-3-amino-piperidin-1-yl)-xanthine (cf. WO 2005/085246, Example 1 (52)):

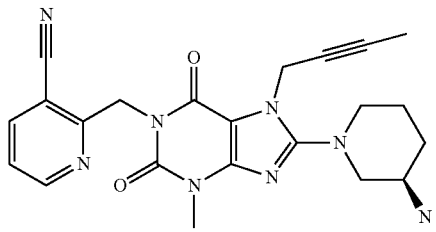 [SMILES: CC#CCn1c(N2CCC[C@@H](N)C2)nc2c1c(=O)n(Cc1ncccc1C#N)c(=O)n2C]

1-[(4-methyl-pyrimidin-2-yl)methyl]-3-methyl-7-(2-butyn-1-yl)-8-((R)-3-amino-piperidin-1-yl)-xanthine (cf. WO 2005/085246, Example 1 (81)):

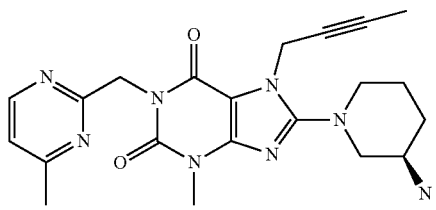 [SMILES: CC#CCn1c(N2CCC[C@@H](N)C2)nc2c1c(=O)n(Cc1nccc(C)n1)c(=O)n2C]

1-[(4,6-dimethyl-pyrimidin-2-yl)methyl]-3-methyl-7-(2-butyn-1-yl)-8-((R)-3-amino-piperidin-1-yl)-xanthine (cf. WO 2005/085246, Example 1 (82)):

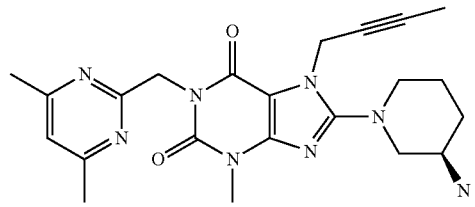 [SMILES: CC#CCn1c(N2CCC[C@@H](N)C2)nc2c1c(=O)n(Cc1nc(C)cc(C)n1)c(=O)n2C]

1-[(quinoxalin-6-yl)methyl]-3-methyl-7-(2-butyn-1-yl)-8-((R)-3-amino-piperidin-1-yl)-xanthine (cf. WO 2005/085246, Example 1 (83)):

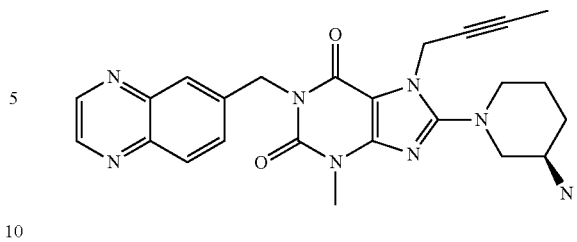

These DPP IV inhibitors are distinguished from structurally comparable DPP IV inhibitors, as they combine exceptional potency and a long-lasting effect with favourable pharmacological properties, receptor selectivity and a favourable side-effect profile or bring about unexpected therapeutic advantages or improvements when combined with other pharmaceutical active substances. Their preparation is disclosed in the publications mentioned.

As different metabolic functional disorders often occur simultaneously, it is quite often indicated to combine a number of different active principles with one another. Thus, depending on the functional disorders diagnosed, improved treatment outcomes may be obtained if a DPP IV inhibitor is combined with an active substance selected from among the other antidiabetic substances, especially active substances that lower the blood sugar level or the lipid level in the blood, raise the HDL level in the blood, lower blood pressure or are indicated in the treatment of atherosclerosis or obesity.

The dosage required of the DPP IV inhibitors when administered intravenously is 0.1 mg to 10 mg, preferably 0.25 mg to 5 mg, and when administered orally 0.5 mg to 100 mg, preferably 2.5 mg to 50 mg, in each case 1 to 4 times a day. For this purpose the compounds, optionally in combination with another active substance, may be formulated together with one or more inert conventional carriers and/or diluents, e.g. with maize starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propylene-glycol, cetylstearylalcohol, carboxymethylcellulose or fatty substances such as hard fat or suitable mixtures thereof, to form conventional galenic preparations such as tablets, coated tablets, capsules, powders, suspensions or suppositories.

The DPP IV inhibitors according to the invention are thus prepared by the skilled man using permitted formulation excipients as described in the prior art. Examples of such excipients are diluents, binders, carriers, fillers, lubricants, flow agents, crystallisation retardants, disintegrants, solubilisers, colourings, pH regulators, surfactants and emulsifiers.

Examples of suitable diluents include cellulose powder, calcium hydrogen phosphate, erythritol, (low-substituted) hydroxypropylcellulose, mannitol, pregelatinised starch or xylitol.

Examples of suitable binders include copolymers of vinylpyrrolidone with other vinyl derivatives (copovidone), hydroxypropylmethylcellulose (HPMC), hydroxypropylcellulose (HPC) polyvinylpyrrolidone (povidone), pregelatinised starch, or low-substituted hydroxypropylcellulose.

Examples of suitable lubricants include talc, polyethyleneglycol, calcium behenate, calcium stearate, hydrogenated castor oil or magnesium stearate.

Examples of suitable disintegrants include maize starch or crospovidone.

Suitable methods of preparing pharmaceutical formulations of the DPP IV inhibitors according to the invention are Direct tabletting of the active substance in powder mixtures with suitable tabletting excipients;

Granulation with suitable excipients and subsequent mixing with suitable excipients and subsequent tabletting as well as film coating; or packing of powder mixtures or granules into capsules.

Suitable granulation methods are wet granulation in the intensive mixer followed by fluidised bed drying;

one-pot granulation;

fluidised bed granulation; or dry granulation (e.g. by roller compaction) with suitable excipients and subsequent tabletting or packing into capsules.

The DPP IV inhibitors mentioned above may also be used in conjunction with other active substances, by means of which improved treatment results can be obtained. Such a combined treatment may be given as a free combination of the substances or in the form of a fixed combination, for example in a tablet or capsule. Pharmaceutical formulations of the combination partner needed for this may either be obtained commercially as pharmaceutical compositions or may be formulated by the skilled man using conventional methods. The active substances which may be obtained commercially as pharmaceutical compositions are described in numerous places in the prior art, for example in the list of drugs that appears annually, the "Rote Liste®" of the federal association of the pharmaceutical industry, or in the annually updated compilation of manufacturers' information on prescription drugs known as the "Physicians' Desk Reference".

Examples of antidiabetic combination partners are metformin; sulphonylureas such as glibenclamide, tolbutamide, glimepiride, glipizide, gliquidon, glibornuride and gliclazide; nateglinide; repaglinide; thiazolidinediones such as rosiglitazone and pioglitazone; PPAR gamma modulators such as metaglidases; PPAR-gamma agonists such as GI 262570; PPAR-gamma antagonists; PPAR-gamma/alpha modulators such as tesaglitazar, muraglitazar and KRP297; PPAR-gamma/alpha/delta modulators; AMPK-activators such as AICAR; acetyl-CoA carboxylase (ACC1 and ACC2) inhibitors; diacylglycerol-acetyltransferase (DGAT) inhibitors; pancreatic beta cell GCRP agonists such as SMT3-receptor-agonists and GPR119; 11β-HSD-inhibitors; FGF19 agonists or analogues; alpha-glucosidase blockers such as acarbose, voglibose and miglitol; alpha2-antagonists; insulin and insulin analogues such as human insulin, insulin lispro, insulin glusilin, r-DNA-insulinaspart, NPH insulin, insulin detemir, insulin zinc suspension and insulin glargin; Gastric inhibitory Peptide (GIP); pramlintide; amylin or GLP-1 and GLP-1 analogues such as Exendin-4; SGLT2-inhibitors such as KGT-1251; inhibitors of protein tyrosine-phosphatase; inhibitors of glucose-6-phosphatase; fructose-1,6-bisphosphatase modulators; glycogen phosphorylase modulators; glucagon receptor antagonists; phosphoenolpyruvatecarboxykinase (PEPCK) inhibitors; pyruvate dehydrogenasekinase (PDK) inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976); glucokinase/regulatory protein modulators incl. glucokinase activators; glycogen synthase kinase inhibitors; inhibitors of the SH2-domain-containing inositol 5-phosphatase type 2 (SHIP2); IKK inhibitors such as high-dose salicylate; JNK1 inhibitors; protein kinase C-theta inhibitors; beta 3 agonists such as ritobegron, YM 178, solabegron, talibegron, N-5984, GRC-1087, rafabegron, FMP825; aldosereductase inhibitors such as AS 3201, zenarestat, fidarestat, epalrestat, ranirestat, NZ-314, CP-744809, and CT-112; SGLT-1 or SGLT-2 inhibitors; KV 1.3 channel inhibitors; GPR40 modulators; SCD-1 inhibitors; CCR-2 antagonists; and other DPP IV inhibitors.

Examples of 11β-HSD1-inhibitors are described in WO 2007/013929, WO 2007/007688, WO 2007/003521, WO 2006/138508, WO 2006/135795, WO 2006/135667, WO 2006/134481, WO 2006/134467, WO 2006/132436, WO 2006/132197, WO 2006/113261, WO 2006/106423, WO 2006/106052, WO 2006/105127, WO 2006/104280, WO 2006/100502, WO 2006/097337, WO 2006/095822, WO 2006/094633, WO 2006/080533, WO 2006/074330, WO 2006/074244, WO 2006/068992, WO 2006/068991, WO 2006/068199, WO 2006/066109, WO 2006/055752, WO 2006/053024, WO 2006/051662, WO 2006/050908, WO 2006/049952, WO 2006/048750, WO 2006/048331, WO 2006/048330, WO 2006/040329, WO 2006/037501, WO 2006/030805, WO 2006/030804, WO 2006/017542, WO 2006/024628, WO 2006/024627, WO 2006/020598, WO 2006/010546, WO 2006/002349, WO 2006/002350, WO 2006/012173, WO 2006/012227, WO 2006/012226, WO 2006/000371, WO 2005/118538, WO 2005/116002, WO 2005/110992, WO 2005/110980, WO 2005/108359, WO 2005/108361, WO 2005/108360, WO 2005/108368, WO 2005/103023, WO 2005/097764, WO 2005/097759, WO 2005/095350, WO 2005/075471, WO 2005/063247, WO 2005/060963, WO 2005/047250, WO 2005/046685, WO 2005/044192, WO 2005/042513, WO 2005/016877, WO 2004/113310, WO 2004/106294, WO 2004/103980, WO 2004/089896, WO 2004/089380, WO 2004/089471, WO 2004/089470, WO 2004/089367, WO 2005/073200, WO 2004/065351, WO 2004/058741, WO 2004/056745, WO 2004/056744, WO 2004/041264, WO 2004/037251, WO 2004/033427, WO 2004/011410, WO 2003/104208, WO 2003/104207, WO 2003/065983, WO 2003/059267, WO 2003/044009, WO 2003/044000, WO 2003/043999, WO 2002/076435, WO 2001/090094, WO 2001/090093, WO 2001/090092, WO 2001/090091, WO 2001/090090, US 2007/049632, US 2006/148871, US 2006/025445, US 2006/004049, US 2005/277647, US 2005/261302, US 2005/245534, US 2005/245532, US 2005/245533 and JP 2005/170939. The foregoing references are hereby incorporated by reference in their entireties. A representative example of an 11β-HSD1-inhibitor is the compound:

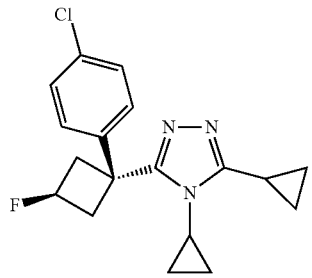 [SMILES: F[C@H]1C[C@](c2ccc(Cl)cc2)(c2nnc(C3CC3)n2C2CC2)C1]

and the salts thereof.

Examples of glycogen phosphorylase modulators are described in WO 2006/126695, WO 2006/082401, WO 2006/082400, WO 2006/059165, WO 2006/059164, WO 2006/059163, WO 2006/056815, WO 2006/055463, WO 2006/055462, WO 2006/055435, WO 2006/053274, WO 2006/052722, WO 2005/085245, WO 2005/085194, WO 2005/073231, WO 2005/073230, WO 2005/073229, WO 2005/067932, WO 2005/020987, WO 2005/020986, WO 2005/020985, WO 2005/019172, WO 2005/018637, WO 2005/013981, WO 2005/013975, WO 2005/012244, WO 2004/113345, WO 2004/104001, WO 2004/096768, WO 2004/092158, WO 2004/078743, WO 2004/072060, WO 2004/

065356, WO 2004/041780, WO 2004/037233, WO 2004/033416, WO 2004/007455, WO 2004/007437, WO 2003/104188, WO 2003/091213, WO 2003/084923, WO 2003/084922, WO 2003/074532, WO 2003/074531, WO 2003/074517, WO 2003/074513, WO 2003/074485, WO 2003/074484, WO 2003/072570, WO 2003/059910, WO 2003/037864, WO 2002/096864, WO 2002/020530, WO 2001/094300, WO 2000/123347, WO 1996/39384, WO 1996/39385, EP 1391460, EP 1136071, EP 1125580, EP 1088824, EP 0978279, JP 2004196702, US 2004/002495, US 2003/195243, and U.S. Pat. No. 5,998,463. The foregoing references are hereby incorporated by reference in their entireties.

Examples of glucokinase-activators are described in WO 2007/017649, WO 2007/007910, WO 2007/007886, WO 2007/007042, WO 2007/007041, WO 2007/007040, WO 2007/006814, WO 2007/006761, WO 2007/006760, WO 2006/125972, WO 2006/125958, WO 2006/112549, WO 2006/059163, WO 2006/058923, WO 2006/049304, WO 2006/040529, WO 2006/040528, WO 2006/016194, WO 2006/016178, WO 2006/016174, WO 2005/121110, WO 2005/103021, WO 2005/095418, WO 2005/095417, WO 2005/090332, WO 2005/080360, WO 2005/080359, WO 2005/066145, WO 2005/063738, WO 2005/056530, WO 2005/054233, WO 2005/054200, WO 2005/049019, WO 2005/046139, WO 2005/045614, WO 2005/044801, WO 2004/081001, WO 2004/076420, WO 2004/072066, WO 2004/072031, WO 2004/063194, WO 2004/063179, WO 2004/052869, WO 2004/050645, WO 2004/031179, WO 2004/002481, WO 2003/095438, WO 2003/080585, WO 2003/055482, WO 2003/047626, WO 2003/015774, WO 2003/000267, WO 2003/000262, WO 2002/048106, WO 2002/046173, WO 2002/014312, WO 2002/008209, WO 2001/085707, WO 2001/085706, WO 2001/083478, WO 2001/083465, WO 2001/044216, and WO 2000/058293. The foregoing references are hereby incorporated by reference in their entireties.

Representative examples of glucokinase-activators are the compounds

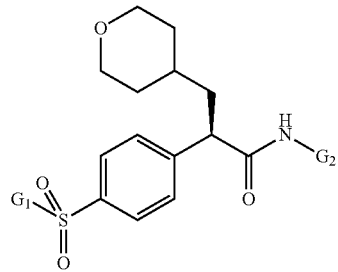

wherein $G_1$ denotes cyclopropyl or cyclobutyl and $G_2$ denotes 5-fluoro-thiazol-2-yl, 1-methyl-1H-pyrazol-3-yl, or pyrazin-2-yl; and

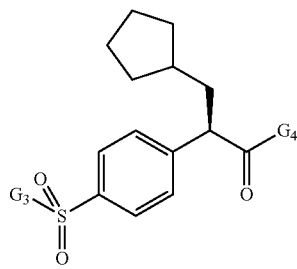

wherein $G_3$ denotes methyl or ethyl and $G_4$ denotes thiazol-2-yl, 4-methyl-thiazol-2-yl, 5-methyl-thiazol-2-yl, or pyrazin-2-yl and the salts thereof.

Examples of SGLT1 or SGLT2-inhibitors are described in WO 2006/108842, WO 2006/087997, WO 2006/080577, WO 2006/080421, WO 2006/073197, WO 2006/064033, WO 2006/062224, WO 2006/054629, WO 2006/037537, WO 2006/035796, WO 2006/018150, WO 2006/008038, WO 2006/002912, WO 2006/010557, WO 2006/011502, WO 2006/011469, WO 2005/121161, WO 2005/012326, WO 2005/095429, WO 2005/095372, WO 2005/095373, WO 2005/092877, WO 2005/085267, WO 2005/085265, WO 2005/085237, WO 2005/063785, WO 2005/021566, WO 2005/012243, WO 2005/012242, WO 2005/012326, WO 2005/012318, WO 2005/011592, WO 2004/113359, WO 2004/099230, WO 2004/089967, WO 2004/089966, WO 2004/087727, WO 2004/080990, WO 2004/058790, WO 2004/052903, WO 2004/052902, WO 2004/019958, WO 2004/018491, WO 2004/014932, WO 2004/014931, WO 2004/013118, WO 2003/099836, WO 2003/080635, WO 2003/020737, WO 2003/011880, WO 2003/000712, WO 2002/098893, WO 2002/088157, WO 2002/083066, WO 2002/068440, WO 2002/068439, WO 2002/064606, WO 2002/053573, WO 2002/044192, WO 2002/036602, WO 2002/028872, WO 2001/074835, WO 2001/074834, WO 2001/068660, WO 2001/027128, WO 2001/016147, JP 2005247834, JP 2004359630, JP 2004196788, JP 2003012686, and US 2006/063722. The foregoing references are hereby incorporated by reference in their entireties.

Representative examples of SGLT1 or SGLT2-inhibitors are the following compounds and the salts or complexes thereof with natural amino acids

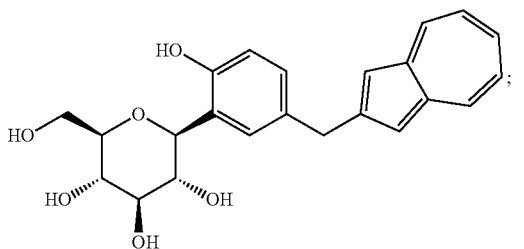

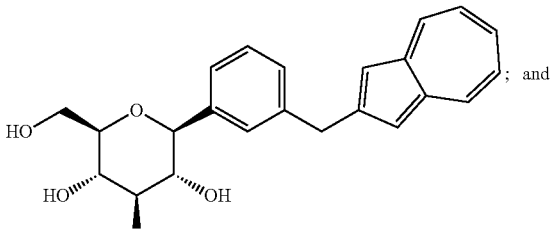

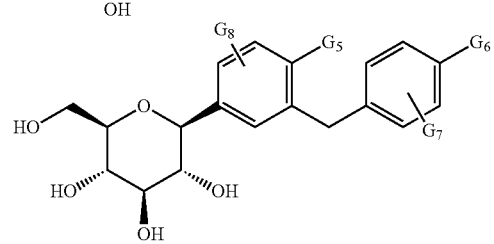

wherein $G_5$ and $G_8$ independently of one another denote hydrogen, fluorine, chlorine, bromine, cyano, methyl, ethyl, isopropyl, difluoromethyl, trifluoromethyl, ethynyl, prop-1-yn-1-yl, but-1-yn-1-yl, hydroxy, methoxy, ethoxy, difluoromethoxy, cyclopropyloxy, cyclobutyloxy, cyclopentyloxy or cyclohexyloxy; and $G_6$ denotes fluorine, chlorine, methyl, ethyl, methoxy, ethoxy, difluoromethoxy, trifluoromethoxy, trimethylsilylethyl, ethynyl, 2-hydroxyprop-2-ylethynyl, 2-methoxyprop-2-ylethynyl, 3-hydroxy-1-propyn-1-yl, 3-methoxy-1-propyn-1-yl, cyclopropyl, cyclobutyl, cyclopentyl, cyclohexyl, cyclopropyloxy, cyclobutyloxy, cyclopentyloxy, cyclohexyloxy, tetrahydrofuran-3-yloxy, tetrahydropyran-4-yloxy, piperidin-4-yloxy, N-methylpiperidin-4-yloxy and N-acetylpiperidin-4-yloxy; and $G_7$ denotes hydrogen or fluorine;

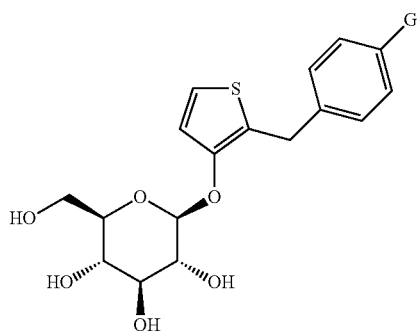

wherein G denotes fluorine, chlorine, methyl, ethyl, ethynyl, methoxy, ethoxy, difluoromethoxy, trifluoromethoxy, cyclobutyloxy, cyclopentyloxy, 3-tetrahydrofuranyloxy, or 4-tetrahydropyranyloxy;

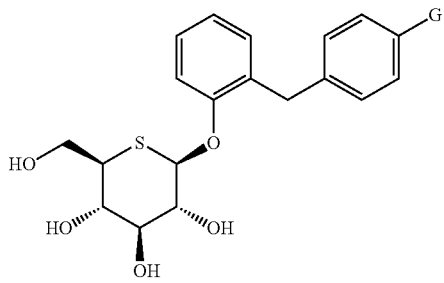

wherein G denotes fluorine, chlorine, methyl, ethyl, ethynyl, methoxy, ethoxy, difluoromethoxy, trifluoromethoxy, cyclobutyloxy, cyclopentyloxy, 3-tetrahydrofuranyloxy, or 4-tetrahydropyranyloxy;

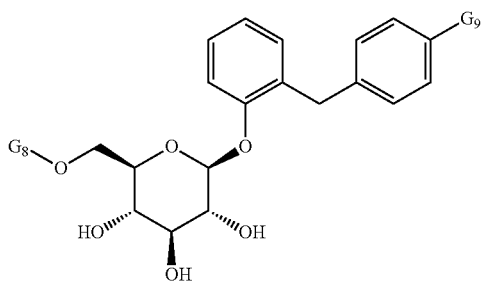

wherein $G_8$ denotes hydrogen, methoxycarbonyl, or ethoxycarbonyl and $G_9$ denotes fluorine, chlorine, methyl, ethyl, ethynyl, methoxy, ethoxy, difluoromethoxy, trifluoromethoxy, cyclobutyloxy, cyclopentyloxy, 3-tetrahydrofuranyloxy, or 4-tetrahydropyranyloxy; and

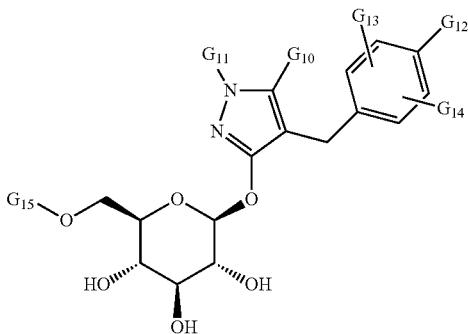

wherein:
$G_{10}$ denotes $C_{1-3}$-alkyl or perfluoro-$C_{1-3}$-alkyl;
$G_{11}$ denotes hydrogen, $C_{1-3}$-alkyl or perfluoro-$C_{1-3}$-alkyl;
$G_{12}$ denotes fluorine, chlorine, bromine, $C_{1-6}$-alkyl, $C_{1-6}$-alkyl substituted by 1 to 3 fluorine atoms, $C_{1-6}$-alkoxy, $C_{1-6}$-alkoxy substituted by 1 to 3 fluorine atoms, $C_{1-6}$-alkylthio, $C_{2-6}$-alkenyl, $C_{2-6}$-alkynyl, perfluoro-$C_{1-3}$-alkyl, cyclobutyloxy, cyclopentyloxy, cyclohexyloxy, tetrahydrofuranyloxy, or 4-tetrahydropyranyloxy; and
$G_{13}$ and $G_{14}$ independently of one another denote hydrogen, fluorine, chlorine, bromine, $C_{1-6}$-alkyl, $C_{1-6}$-alkyl substituted by 1 to 3 fluorine atoms, $C_{1-6}$-alkoxy, $C_{1-6}$-alkoxy substituted by 1 to 3 fluorine atoms, $C_{1-6}$-alkylthio, $C_{2-6}$-alkenyl, $C_{2-6}$-alkynyl, perfluoro-$C_{1-3}$-alkyl; and
$G_{15}$ denotes hydrogen, $C_{2-20}$-alkanoyl, $C_{1-6}$-alkoxycarbonyl or benzoyl.

A particularly preferred example of an antidiabetic combination partner is metformin in doses of about 100 mg to 500 mg or 200 mg to 850 mg (1-3 times a day), or about 300 mg to 1000 mg once or twice a day, or delayed-release metformin in doses of about 100 mg to 1000 mg or preferably 500 mg to 1000 mg once or twice a day or about 500 mg to 2000 mg once a day. Another particularly preferred example is pioglitazone in a dosage of about 1-10 mg, 15 mg, 30 mg, or 45 mg once a day. Another particularly preferred example is miglitol in a dosage of about 10 mg to 50 mg or up to 100 mg 1-3 times a day.

Examples of combination partners that lower the lipid level in the blood are HMG-CoA-reductase inhibitors such as simvastatin, atorvastatin, lovastatin, fluvastatin, pravastatin and rosuvastatin; fibrates such as bezafibrate, fenofibrate, clofibrate, gemfibrozil, etofibrate and etofyllinclofibrate; nicotinic acid and the derivatives thereof such as acipimox; PPAR-alpha agonists; PPAR-delta agonists; inhibitors of acyl-coenzyme A:cholesterolacyltransferase (ACAT; EC 2.3.1.26) such as avasimibe; cholesterol resorption inhibitors such as ezetimib; substances that bind to bile acid, such as cholestyramine, colestipol and colesevelam; inhibitors of bile acid transport; HDL modulating active substances such as D4F, reverse D4F, LXR modulating active substances and FXR modulating active substances; CETP inhibitors such as torcetrapib, JTT-705 or compound 12 from WO 2007/005572; LDL receptor modulators; and ApoB100 antisense RNA. A particularly preferred example is atorvastatin in a dosage of about 1 mg to 40 mg or 10 mg to 80 mg once a day.

Examples of combination partners that lower blood pressure are beta-blockers such as atenolol, bisoprolol, celiprolol, metoprolol and carvedilol; diuretics such as hydrochlorothiazide, chlortalidon, xipamide, furosemide, piretanide, torasemide, spironolactone, eplerenone, amiloride and triamterene; calcium channel blockers such as amlodipine, nifedipine, nitrendipine, nisoldipine, nicardipine, felodipine, lacidipine, lercanipidine, manidipine, isradipine, nilvadipine, verapamil, gallopamil and diltiazem; ACE inhibitors such as ramipril, lisinopril, cilazapril, quinapril, captopril, enalapril, benazepril, perindopril, fosinopril and trandolapril; as well as angiotensin II receptor blockers (ARBs) such as telmisartan, candesartan, valsartan, losartan, irbesartan, olmesartan and eprosartan. Particularly preferred examples are metoprolol in a dosage of 50 mg to 200 mg per day, Amlodipin in a dosage of 2.5 mg to 10 mg per day, ramipril in a dosage of 2.5 mg to 15 mg per day, valsartan in a dosage of 80 to 160 mg per day, and telmisartan in a dosage of 20 mg to 320 mg or 40 mg to 160 mg per day.

Examples of combination partners which increase the HDL level in the blood are Cholesteryl Ester Transfer Protein (CETP) inhibitors; inhibitors of endothelial lipase; regulators of ABC1; LXRalpha antagonists; LXRbeta agonists; PPAR-delta agonists; LXRalpha/beta regulators, and substances that increase the expression and/or plasma concentration of apo-lipoprotein A-I.

Examples of combination partners for the treatment of obesity are sibutramine; tetrahydrolipstatin (orlistat); alizyme; dexfenfluramine; axokine; cannabinoid receptor 1 antagonists such as the CB1 antagonist rimonobant; MCH-1 receptor antagonists; MC4 receptor agonists; NPY5 as well as NPY2 antagonists; beta3-AR agonists such as SB-418790 and AD-9677; 5HT2c receptor agonists such as APD 356; myostatin inhibitors; Acrp30 and adiponectin; steroyl CoA desaturase (SCD1) inhibitors; fatty acid synthase (FAS) inhibitors; CCK receptor agonists; Ghrelin receptor modulators; Pyy 3-36; orexin receptor antagonists; and tesofensine.

Examples of combination partners for the treatment of atherosclerosis are phospholipase A2 inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976); oxLDL antibodies and oxLDL vaccines; apoA-1 Milano; ASA; and VCAM-1 inhibitors.

Examples of combination partners for the treatment of heart failure are beta-blockers such as atenolol, bisoprolol, celiprolol, and metoprolol; diuretics such as hydrochlorothiazide, chlortalidone, xipamide, furosemide, piretanide, torasemide, spironolactone, eplerenone, amiloride and triamterene; ACE inhibitors such as ramipril, lisinopril, cilazapril, quinapril, captopril, enalapril, benazepril, perindopril, fosinopril and trandolapril; as well as angiotensin II receptor blockers (ARBs) such as telmisartan, candesartan, valsartan, losartan, irbesartan, olmesartan and eprosartan; heart glycosides such as digoxin and digitoxin; combined alpha/beta-blockers such as carvedilol; B-type natriuretic peptide (BNP) and BNP-derived peptides and BNP-fusion products. Particularly preferred examples are metoprolol in a dosage of 50 mg to 200 mg per day, ramipril in a dosage of 2.5 mg to 15 mg per day, valsartan in a dosage of 80 to 160 mg per day, telmisartan in a dosage of 20 mg to 320 mg or 40 mg to 160 mg per day, eplereron in a dosage of 25-100 mg, digoxin in a dosage of 0.25 mg to 0.6 mg per day carvedilol in a dosage of 3.25 mg to 100 mg, BNP (e.g. nesiritide) in a dosage of 2 µg/kg as a bolus followed by 0.01 µg/kg/min.

Drug combinations comprising the selected DPP IV inhibitors contain for example 1.75 mg to 10.5 mg glibenclamide, 500 mg to 3000 mg tolbutamide, 0.5-6 g glimepiride, 2.5 mg to 40 mg glipizide, 1-4×30 mg gliquidone, to 3×25 mg glibornuride, 80 mg to 160 mg gliclazide; 500 mg to 1000 mg, preferably 500 mg, 850 mg or 1000 mg metformin; 60 mg to 180 mg nateglinide; 0.25 mg to 4 mg repaglinide; 2 mg to 45 mg thiazolidinedione; 200 mg to 600 mg metaglidases; 2.5 mg to 5 mg PPAR gamma/alpha modulators; 0.1 mg to 100 mg alpha glucosidase blocker; 1-250 IU insulin; 15 µg to 120 µg Pramlintide; 5 mg to 80 mg statin; 50 mg to 1000 mg fibrate; 1000 mg to 3000 mg nicotinic acid or derivative; about 250 mg acipimox; about 10 mg of a cholesterol resorption inhibitor; 0.5 g to 30 g of a bile acid binding substance; 10 mg to 600 mg and preferably 10 mg to 120 mg CETP inhibitor; 2.5 mg to 100 mg beta-blocker; 3 mg to 200 mg diuretic; 2.5 mg to 500 mg calcium channel blocker; 1 mg to 40 mg ACE inhibitor; 5 mg to 600 mg angiotensin II receptor blocker; 10 mg to 15 mg sibutramine; about 120 mg orlistat; 15 mg to 30 mg dexfenfluramine; or 5 mg to 20 mg cannabinoid receptor antagonist, eplerenone in a dosage of 25 mg to 100 mg; digoxin in a dosage of 0.25 mg to 0.6 mg per day; carvedilol in a dosage of 3.25 mg to 100 mg; BNP (e.g. nesiritide) in a dosage of 2 µg/kg as a bolus followed by 0.01 µg/kg/min.

EXAMPLES

Example 1

Treatment of Pre-Diabetes

The efficacy of a DPPIV inhibitor according to the invention in the treatment of pre-diabetes characterised by pathological fasting glucose and/or impaired glucose tolerance can be tested using clinical studies. In studies over a shorter period (e.g. 2-4 weeks) the success of the treatment is examined by determining the fasting glucose values and/or the glucose values after a meal or after a loading test (oral glucose tolerance test or food tolerance test after a defined meal) after the end of the period of therapy for the study and comparing them with the values before the start of the study and/or with those of a placebo group. In addition, the fructosamine value can be determined before and after therapy and compared with the initial value and/or the placebo value. A significant drop in the fasting or non-fasting glucose levels demonstrates the efficacy of the treatment. In studies over a longer period (12 weeks or more) the success of the treatment is tested by determining the HbA1c value, by comparison with the initial value and/or with the value of the placebo group. A significant change in the HbA1c value compared with the initial value and/or the placebo value demonstrates the efficacy of the DPP IV inhibitor for treating pre-diabetes.

Example 2

Preventing Manifest Type 2 Diabetes

Treating patients with pathological fasting glucose and/or impaired glucose tolerance (pre-diabetes) is also in pursuit of the goal of preventing the transition to manifest type 2 diabetes. The efficacy of a treatment can be investigated in a comparative clinical study in which pre-diabetes patients are treated over a lengthy period (e.g. 1-5 years) with either an active substance or a combination of active substances or with placebo or with a non-drug therapy or other medicaments. During and at the end of the therapy, by determining the fasting glucose and/or a loading test (e.g. oGTT), a check is made to determine how many patients exhibit manifest type 2 diabetes, i.e. a fasting glucose level of >125 mg/dl and/or a 2 h value according to oGTT of >199 mg/dl. A significant reduction in the number of patients who exhibit manifest type 2 diabetes when treated with active substance or a combination of active substances as compared to one of the other forms of treatment, demonstrates the efficacy of the active substance or combination of active substances in preventing a transition from pre-diabetes to manifest diabetes.

Example 3

Treatment of Type 2 Diabetes

Treating patients with type 2 diabetes with the active substances according to the invention, in addition to producing an acute improvement in the glucose metabolic situation, prevents a deterioration in the metabolic situation in the long term. This can be observed is patients are treated for a longer period, e.g. 1-6 years, with the active substances or combinations of active substances according to the invention and are compared with patients who have been treated with other antidiabetic medicaments. There is evidence of therapeutic success compared with patients treated with other antidiabetic medicaments if no or only a slight increase in the fasting glucose and/or HbA1c value is observed. Further evidence of therapeutic success is obtained if a significantly smaller percentage of the patients treated with an active substance according to the invention or a combination of active substances according to the invention, compared with patients who have been treated with other medicaments, undergo a deterioration in the glucose metabolic position (e.g. an increase in the HbA1c value to >6.5% or >7%) to the point where treatment with an additional oral antidiabetic medicament or with insulin or with an insulin analogue or with another antidiabetic agent (e.g. GLP-1 analogue) is indicated.

Example 4

Treatment of Insulin Resistance

In clinical studies running for different lengths of time (e.g. 2 weeks to 12 months) the success of the treatment is checked using a hyperinsulinaemic euglycaemic glucose clamp study. A significant rise in the glucose infusion rate at the end of the study, compared with the initial value or compared with a placebo group, or a group given a different therapy, proves the efficacy of an active substance or combination of active substances in the treatment of insulin resistance.

Example 5

Treatment of Diabetic Hyper- or Dyslipidaemia

In clinical studies running for different lengths of time (e.g. 2 weeks to 60 months) on patients with type 2 diabetes the success of the treatment is checked by determining the total cholesterol, LDL-cholesterol, HDL-cholesterol, and plasma triglycerides. A significant fall in the total cholesterol, LDL-cholesterol, or plasma triglycerides and/or a rise in the HDL-cholesterol levels during or at the end of the study, compared with the initial value or compared with a placebo group, or a group given a different therapy, proves the efficacy of an active substance or combination of active substances in the treatment of diabetic dys- or hyperlipidaemia.

Example 6

Treatment of Hyperglycaemia

In clinical studies running for different lengths of time (e.g. 1 day to 24 months) the success of the treatment in patients with hyperglycaemia is checked by determining the fasting glucose or non-fasting glucose (e.g. after a meal or a loading test with oGTT or a defined meal). A significant fall in these glucose values during or at the end of the study, compared with the initial value or compared with a placebo group, or a group given a different therapy, proves the efficacy of an active substance or combination of active substances in the treatment of hyperglycaemia.

Example 7

Treatment of Gestational Diabetes

In clinical studies running for a shorter period (e.g. 2-4 weeks) the success of the treatment is checked by determining the fasting glucose values and/or the glucose values after a meal or after a loading test (oral glucose tolerance test or food tolerance test after a defined meal) at the end of the therapeutic period of the study and comparing them with the values before the start of the study and/or with those of a placebo group. In addition, the fructosamine value can be determined before and after treatment and compared with the initial value and/or a placebo value. A significant fall in the fasting or non-fasting glucose levels demonstrates the efficacy of an active substance or combination of active substances.

In longer-running studies (12 weeks or more) the success of the treatment is checked by determining the HbA1c value (compared with initial value and placebo group). A significant change in the HbA1c value compared with the starting value and/or placebo value demonstrates the efficacy of an active substance or combination of active substances in the treatment of gestational diabetes.

Example 8

Treatment of Women Who have Had Gestational Diabetes

Patients with gestational diabetes have a significantly increased risk of contracting manifest type 2 diabetes after the pregnancy. Therapy may be provided with the objective of preventing the transition to manifest type 2. For this purpose, women with a history of gestational diabetes are treated either with an active substance according to the invention or a combination of active substances according to the invention or with placebo or with a non-drug therapy or with other medicaments, over a lengthy period (e.g. 1-4 years). During and at the end of the treatment a check is carried out by determining the fasting glucose and/or by a loading test (e.g. oGTT) to see how many patients have developed manifest type 2 diabetes (fasting glucose level>125 mg/dl and/or 2 h value after oGTT>199 mg/dl). A significant reduction in the number of patients who develop manifest type 2 diabetes when treated with an active substance according to the invention or a combination of active substances according to the invention, compared with a different type of therapy, is proof of the efficacy of an active substance or a combination of active substances in preventing manifest diabetes in women with a history of gestational diabetes.

Example 9

Prevention of Micro- or Macrovascular Complications

The treatment of type 2 diabetes or pre-diabetes patients with an active substance according to the invention or a combination of active substances according to the invention prevents or reduces microvascular complications (e.g. diabetic neuropathy, diabetic retinopathy, diabetic nephropathy, diabetic foot, diabetic ulcer) or macrovascular complications (e.g. myocardial infarct, acute coronary syndrome, unstable angina pectoris, stable angina pectoris, stroke, peripheral arterial occlusive disease, cardiomyopathy, heart failure, heart rhythm disorders, vascular restenosis). Type 2 diabetes or patients with pre-diabetes are treated long-term, e.g. for 1-6 years, with an active substance according to the invention or a combination of active substances according to the invention and compared with patients who have been treated with other antidiabetic medicaments or with placebo. Evidence of the therapeutic success compared with patients who have been treated with other antidiabetic medicaments or with placebo can be found in the smaller number of single or multiple complications. In the case of macrovascular events, diabetic foot and/or diabetic ulcer, the numbers are counted by anamnesis and various test methods. In the case of diabetic retinopathy the success of the treatment is determined by computer-controlled illumination and evaluation of the background to the eye or other ophthalmic methods. In the case of diabetic neuropathy, in addition to anamnesis and clinical examination, the nerve conduction rate can be measured using a calibrated tuning fork, for example. With regard to diabetic nephropathy the following parameters may be investigated before the start, during and at the end of the study: secretion of albumin, creatinin clearance, serum creatinin values, time taken for the serum creatinin values to double, time taken until dialysis becomes necessary.

Example 10

Treatment of Metabolic Syndrome

The efficacy of the active substances or combinations of active substances according to the invention can be tested in clinical studies with varying run times (e.g. 12 weeks to 6 years) by determining the fasting glucose or non-fasting glucose (e.g. after a meal or a loading test with oGTT or a defined meal) or the HbA1c value. A significant fall in these glucose values or HbA1c values during or at the end of the study, compared with the initial value or compared with a placebo group, or a group given a different therapy, proves the efficacy of an active substance or combination of active substances in the treatment of Metabolic Syndrome. Examples of this are a reduction in systolic and/or diastolic blood pressure, a lowering of the plasma triglycerides, a reduction in total or LDL cholesterol, an increase in HDL cholesterol or a reduction in weight, either compared with the starting value at the beginning of the study or in comparison with a group of patients treated with placebo or a different therapy.

Example 11

DPPIV Inhibitor Film-Coated Tablets

In order to prepare a granulating solution, copovidone is dissolved in purified water at ambient temperature. DPP IV inhibitor, mannitol, pre-gelatinised starch and maize starch are mixed in a suitable mixer in order to prepare a premix. The premix is moistened with the granulating solution and then granulated in a mixer with a high shear rate. The moist granules are screened through a screen with a mesh size of 1.6 mm. The granules are dried at about 60° C. in a fluidised bed dryer until a loss in drying value of 2-4% is obtained. The finished mixture is compressed to form tablet cores.

In a suitable mixer, hydroxypropylmethyl-cellulose, polyethyleneglycol, talc, titanium dioxide and iron oxide are suspended in purified water at ambient temperature to prepare a suspension for the tablet coating. The tablet cores are coated with this suspension until a weight increase of 3% is obtained. For example, the following tablet compositions may be obtained in this way:

| Ingredient | mg | mg | mg | mg | mg |
|---|---|---|---|---|---|
| DPP IV inhibitor | 0.500 | 1.000 | 2.500 | 5.000 | 10.000 |
| mannitol | 67.450 | 66.950 | 65.450 | 130.900 | 125.900 |
| pre-gelatinised starch | 9.000 | 9.000 | 9.000 | 18.000 | 18.000 |
| maize starch | 9.000 | 9.000 | 9.000 | 18.000 | 18.000 |
| copovidone | 2.700 | 2.700 | 2.700 | 5.400 | 5.400 |
| magnesium stearate | 1.350 | 1.350 | 1.350 | 2.700 | 2.700 |
| Total mass (tablet core) | 90.000 | 90.000 | 90.000 | 180.000 | 180.000 |
| HPMC | 1.500 | 1.500 | 1.500 | 2.500 | 2.500 |
| PEG | 0.150 | 0.150 | 0.150 | 0.250 | 0.250 |
| titanium dioxide | 0.750 | 0.750 | 0.750 | 1.250 | 1.250 |
| talc | 0.525 | 0.525 | 0.525 | 0.875 | 0.875 |
| iron oxide, yellow | 0.075 | 0.075 | 0.075 | 0.125 | 0.125 |
| Total mass (film-coated tablet) | 93.000 | 93.000 | 93.000 | 185.000 | 185.000 |

Example 12

Enhancing the Vitality and Secretion Capacity of Islets of Langerhans or Beta Cells This is done after successful isolation of the islets of Langerhans or pancreatic beta cells, by storing them, transporting them or cultivating them in a medium which contains DPP IV inhibitors in a concentration of 1 nmol/l to 1 μmmol/l, preferably in a concentration of 1 nmol/l and 100 nmol/l, for future transplantation.

In addition, after transplantation with islets of Langerhans or pancreatic beta cells, the patients (and these may also be animals) are treated with DPP IV inhibitors in a daily dosage of between 1 mg and 200 mg, preferably with a dose of 5 mg and 100 mg of a DPP IV inhibitor, in order to enhance the vitality and secretion capacity of the transplant. This is tested either by analysis of the insulin secretion after stimulation with glucose or another agent that increases insulin secretion. Moreover, the improvement in the quality may also be checked in vitro or in animal models using the TUNEL technique, which is described in Diabetologia 42:566, 1999 or Diabetes 48:738, 1999 (investigation of apoptosis and inhibition thereof).

Example 13

Combined Treatment with DPP IV Inhibitor—Metformin

For treating type 2 diabetes or pre-diabetes a DPP IV inhibitor according to the invention may be combined with the anti-diabetically active substance metformin, either in a free combination or in a fixed combination in a tablet. A therapeutically effective dose of the DPP IV inhibitor (e.g. a dose of between 0.1 and 100 mg) may be combined with different doses of metformin, e.g. with 500 mg, 850 mg or 1000 mg metformin as a single dose with a total daily dose of metformin of 500-2850 mg, or with 500 mg, 1000 mg, 1500 mg, or 2000 mg metformin in delayed-release form. The clinical efficacy of such a combination with metformin can be tested in a clinical study. For this, patients with type 2 diabetes or with pre-diabetes are treated either with a DPP IV inhibitor on its own or with metformin on its own or with a combination von DPP IV inhibitor and metformin. The treatment lasts between 2 weeks and 6 years. Evidence that the combination is appropriate and effective can be found in the fact that the combination of a DPP-IV inhibitor with metformin leads to a significantly greater reduction in the fasting glucose and/or non-fasting glucose and/or the HbA1c value than either the DPP IV inhibitor alone or metformin alone.

Example 14

Combined Treatment with DPP IV Inhibitor—Glitazone

For treating type 2 diabetes or pre-diabetes a DPP IV inhibitor according to the invention may be combined with the anti-diabetically active substance group comprising the glitazones or thiazolidinediones (e.g. pioglitazone or rosiglitazone), either in a free combination or in a fixed combination in a tablet. A therapeutically effective dose of the DPP IV inhibitor (e.g. a dose of between 0.1 and 100 mg) may be combined with different doses of pioglitazone (15 mg, 30 mg, or 45 mg) or rosiglitazone (2 mg, 4 mg or 8 mg, given either once or twice a day). The clinical efficacy of such a combination with rosiglitazone or pioglitazone can be tested in a clinical study. For this, patients with type 2 diabetes or with pre-diabetes are treated either with a DPP IV inhibitor on its own or with rosiglitazone or pioglitazone alone or with a combination of DPP IV inhibitor and rosiglitazone or pioglitazone. The treatment lasts between 2 weeks and 6 years. Evidence that the combination is appropriate and effective can be found in the fact that the combination of a DPP-IV inhibitor with rosiglitazone or pioglitazone leads to a significantly greater reduction in the fasting glucose and/or non-fasting glucose and/or the HbA1c value than either the DPP IV inhibitor alone or rosiglitazone or pioglitazone alone.

Example 15

Combined Treatment with DPP IV Inhibitor—SGLT2 Inhibitor

For treating type 2 diabetes or pre-diabetes a DPP IV inhibitor according to the invention may be combined with the anti-diabetically active substance group comprising the SGLT-2 inhibitors, either in a free combination or in a fixed combination in a tablet. A therapeutically effective dose of the DPP IV inhibitor (e.g. a dose of between 0.1 and 100 mg) may be combined with different doses of SGLT-2 inhibitor (0.5 mg to 1000 mg). The clinical efficacy of such a combination with SGLT-2 inhibitor can be tested in a clinical study. For this, patients with type 2 diabetes or with pre-diabetes are treated either with a DPP IV inhibitor on its own or with a SGLT-2 inhibitor on its own or with a combination of DPP IV inhibitor and SGLT-2 inhibitor. The treatment lasts between 2 weeks and 6 years. Evidence that the combination is appropriate and effective can be found in the fact that the combination of a DPP-IV inhibitor with the SGLT-2 inhibitor leads to a significantly greater reduction in the fasting glucose and/or non-fasting glucose and/or the HbA1c value than either the DPP IV inhibitor alone or the SGLT-2 inhibitor alone.

Example 16

Combined Treatment with DPP IV Inhibitor—Antihypertensive

For treating a patient with type 2 diabetes or pre-diabetes or with Metabolic Syndrome a DPP IV inhibitor according to the invention may be combined with an anti-hypertensively active substance, either in a free combination or in a fixed combination in a tablet. A therapeutically effective dose of the DPP IV inhibitor (e.g. a dose of between 0.1 and 100 mg) may be combined with different doses of ACE-inhibitors (e.g. 2.5 mg to 15 mg ramipril), AT1-receptor-antagonists (e.g. 20 mg to 160 mg telmisartan), beta-blockers (e.g. 50 mg to 200 mg metoprolol), or diuretics (e.g. 12.5 mg to 25 mg hydrochlorothiazide). The clinical efficacy of such a combination with antihypertensives can be tested in a clinical study. For this, patients with type 2 diabetes or with pre-diabetes or with Metabolic Syndrome are treated either with a DPP IV inhibitor on its own or with an antihypertensive on its own or with a combination of DPP IV inhibitor and antihypertensive. The treatment lasts between 2 weeks and 6 years. Evidence that the combination is appropriate and effective can be found in the fact that the combination of a DPP-IV inhibitor with the antihypertensive lowers the fasting glucose and/or non-fasting glucose and/or the HbA1c value at least as much as the DPP IV inhibitor alone, and if the combination of the DPP-IV inhibitor with the antihypertensive lowers the systolic and/or diastolic arterial blood pressure at least as much as the antihypertensive alone.

Example 17

Combined Treatment with DPP IV Inhibitor—Lipid Lowering Agent

For treating a patient with type 2 diabetes or pre-diabetes or with Metabolic Syndrome or with diabetic dys- or hyperlipidaemia, a DPP IV inhibitor according to the invention may be combined with a lipid lowering agent/HDL-raising agent, either in a free combination or in a fixed combination in a tablet. A therapeutically effective dose of the DPP IV inhibitor (e.g. a dose of between 0.1 and 100 mg) may be combined with different doses of statins (e.g. 10 mg to 80 mg atorvastatin or 10 mg to 80 mg simvastatin), fibrates (e.g. fenofibrate), cholesterol absorption inhibitors, or with HDL-raising substances such as CETP-inhibitors (e.g. torcetrapib 10 mg to 120 mg once a day or 120 mg twice a day). The clinical efficacy of such a combination with lipid lowering agents/HDL-raising agents can be tested in a clinical study. For this, patients with type 2 diabetes or with pre-diabetes or with Metabolic Syndrome or with diabetic dys- or hyperlipidaemia are treated either with a DPP IV inhibitor on its own or with a lipid lowering agent/HDL-raising agent on its own or with a combination of DPP IV inhibitor and lipid lowering agent/HDL-raising agent. The treatment lasts between 2 weeks and 6 years. Evidence that the combination is appropriate and effective can be found in the fact that the combination of the DPP-IV inhibitor with the lipid lowering agent/HDL-raising agent lowers the fasting glucose and/or non-fasting glucose and/or the HbA1c value at least as much as the DPP IV inhibitor alone, and if the combination of the DPP-IV inhibitor with a lipid lowering agent/HDL-raising agent lowers the total cholesterol or LDL-cholesterol or plasma triglycerides at least as much or increases the HDL-cholesterol value at least as much as the lipid lowering agent/HDL-raising agent alone.

Example 18

Combined Treatment of DPP IV Inhibitor—BNP/BNP-Derived Peptides or BNP-Fusion Peptides in Patients with Heart Failure For treating a patient with acute heart failure, a DPP IV inhibitor according to the invention may be combined with a substance that favourably affects heart failure, either in a free combination or in a fixed combination in a tablet. A therapeutically effective dose of the DPP IV inhibitor (e.g. a dose of between 0.1 and 100 mg) may be combined with different doses of ACE-inhibitors (e.g. 2.5 mg to 15 mg ramipril), AT1-receptor-antagonists (e.g. 20 mg to 160 mg telmisartan), beta-blockers (e.g. 50 mg to 200 mg metoprolol), combined alpha/beta-blockers (e.g. 3.25 mg to 100 mg carvedilol), diuretics (e.g. 12.5 mg to 25 mg hydrochlorothiazide), mineralocorticoid receptor antagonists (e.g. 25 mg to 100 mg eplerenone; and/or B-type natriuretic peptide (BNP) (e.g. 2 µg/kg as a bolus followed by 0.01 µg/kg/min nesiritide), a BNP-derived peptide or a BNP-fusion product. The combination of BNP and DPP-IV inhibitor leads to a higher concentration of full length BNP (1-32) in vivo. The clinical efficacy of the combinations specified can be tested in clinical studies. The treatment lasts between 1 day and 6 years. Evidence that the combination is effective in treating acute heart failure can be found in the fact that compared with other therapies the combination leads to a significant improvement in the clinical situation (higher cardiac ejection output and/or reversal of pulmonary congestion, and/or reversal of pulmonary wedge pressure, and/or a reduction in mortality caused by acute heart failure).

Example 19

Treatment with DPP-IV Inhibitor in Patients with Heart Failure

A DPP IV inhibitor according to the invention may be used to treat a patient with chronic heart failure. This treatment leads to a higher concentration of endogenous full length BNP (1-32) in vivo. The clinical efficacy of this treatment is tested in clinical studies. The treatment lasts between 2 weeks and 6 years. Evidence that the combination is effective in treating chronic heart failure can be found in the fact that a DPP-IV inhibitor according to the invention leads to a significant improvement in the clinical situation compared with a different treatment or placebo (less frequent hospitalisation due to acute heart failure, the ability to walk longer distances, a higher loadability in ergometrics, a higher cardiac ejection output and/or reversal of pulmonary congestion, and/or a reduction in mortality caused by heart failure).

What is claimed is:

1. A method of treating type II diabetes mellitus comprising administering to a patient in need thereof a pharmaceutically effective oral amount of 1-[(4-methyl-quinazolin-2-yl)-methyl]-3-methyl-7-(2-butyn-1-yl)-8-(3-(R)-amino-piperidin-1-yl)-xanthine, and a pharmaceutically effective amount of metformin, which is from 300 mg to 1000 mg once or twice a day, or delayed-release metformin in a dose of 500 mg to 1000 mg once or twice a day or 500 mg to 2000 mg once a day.

2. The method according to claim 1, wherein the pharmaceutically effective oral amount of 1-[(4-methyl-quinazolin-2-yl)methyl]-3-methyl-7-(2-butyn-1-yl)-8-(3-(R)-amino-piperidin-1-yl)-xanthine is an oral daily dose of from 2.5 mg to 10 mg.

3. The method according to claim 1, wherein the 1-[(4-methyl-quinazolin-2-yl)methyl]-3-methyl-7-(2-butyn-1-yl)-8-(3-(R)-amino-piperidin-1-yl)-xanthine is administered in an oral dosage of from 0.5 mg to 50 mg.

4. The method according to claim 1, wherein the 1-[(4-methyl-quinazolin-2-yl)methyl]-3-methyl-7-(2-butyn-1-yl)-8-(3-(R)-amino-piperidin-1-yl)-xanthine is administered in an oral dosage of from 2.5 mg to 10 mg.

5. The method according to claim 1, wherein the 1-[(4-methyl-quinazolin-2-yl)methyl]-3-methyl-7-(2-butyn-1-yl)-8-(3-(R)-amino-piperidin-1-yl)-xanthine is administered in an oral dosage of 0.5 mg, 1 mg, 2.5 mg, 5 mg or 10 mg.

6. The method according to claim 1, wherein the 1-[(4-methyl-quinazolin-2-yl)methyl]-3-methyl-7-(2-butyn-1-yl)-8-(3-(R)-amino-piperidin-1-yl)-xanthine is administered in an oral dosage of 1 mg, 2.5 mg or 5 mg.

7. The method according to claim 1, wherein the 1-[(4-methyl-quinazolin-2-yl)methyl]-3-methyl-7-(2-butyn-1-yl)-8-(3-(R)-amino-piperidin-1-yl)-xanthine is administered in an oral dosage of 2.5 mg or 5 mg.

8. The method according to claim 1, wherein the 1-[(4-methyl-quinazolin-2-yl)methyl]-3-methyl-7-(2-butyn-1-yl)-8-(3-(R)-amino-piperidin-1-yl)-xanthine is administered in an oral dosage of from 2.5 mg to 50 mg.

9. The method according to claim 1, wherein the 1-[(4-methyl-quinazolin-2-yl)methyl]-3-methyl-7-(2-butyn-1-yl)-8-(3-(R)-amino-piperidin-1-yl)-xanthine is administered in an oral daily dose of 5 mg.

10. A method of treating type 2 diabetes or pre-diabetes comprising administering to a patient in need thereof a therapeutically effective oral dose of 1-[(4-methyl-quinazolin-2-yl)methyl]-3-methyl-7-(2-butyn-1-yl)-8-(3-(R)-amino-piperidin-1-yl)-xanthine in combination with a therapeutically effective dose of metformin, which is 500 mg, 850 mg or 1000 mg metformin as a single dose with a total daily dose of metformin of 500-2850 mg, or which is 500 mg, 1000 mg, 1500 mg or 2000 mg metformin in delayed release form.

11. The method according to claim 10, wherein the 1-[(4-methyl-quinazolin-2-yl)methyl]-3-methyl-7-(2-butyn-1-yl)-8-(3-(R)-amino-piperidin-1-yl)-xanthine is administered in an oral dosage of from 0.5 mg to 50 mg.

12. The method according to claim 10, wherein the 1-[(4-methyl-quinazolin-2-yl)methyl]-3-methyl-7-(2-butyn-1-yl)-8-(3-(R)-amino-piperidin-1-yl)-xanthine is administered in an oral dosage of from 2.5 mg to 10 mg.

13. The method according to claim 10, wherein the 1-[(4-methyl-quinazolin-2-yl)methyl]-3-methyl-7-(2-butyn-1-yl)-8-(3-(R)-amino-piperidin-1-yl)-xanthine is administered in an oral dosage of 0.5 mg, 1 mg, 2.5 mg, 5 mg or 10 mg.

14. The method according to claim 10, wherein the 1-[(4-methyl-quinazolin-2-yl)-methyl]-3-methyl-7-(2-butyn-1-yl)-8-(3-(R)-amino-piperidin-1-yl)-xanthine is administered in an oral dosage of 1 mg, 2.5 mg or 5 mg.

15. The method according to claim 10, wherein the 1-[(4-methyl-quinazolin-2-yl)-methyl]-3-methyl-7-(2-butyn-1-yl)-8-(3-(R)-amino-piperidin-1-yl)-xanthine is administered in an oral dosage of 2.5 mg or 5 mg.

16. The method according to claim 10, wherein the 1-[(4-methyl-quinazolin-2-yl)-methyl]-3-methyl-7-(2-butyn-1-yl)-8-(3-(R)-amino-piperidin-1-yl)-xanthine is administered in an oral dosage of from 2.5 mg to 50 mg.

17. The method according to claim 10, wherein the 1-[(4-methyl-quinazolin-2-yl)-methyl]-3-methyl-7-(2-butyn-1-yl)-8-(3-(R)-amino-piperidin-1-yl)-xanthine is administered in an oral daily dose of 5 mg.

18. A method of treating type II diabetes mellitus comprising administering to a patient in need thereof a pharmaceutically effective oral amount of 1-[(4-methyl-quinazolin-2-yl)-methyl]-3-methyl-7-(2-butyn-1-yl)-8-(3-(R)-amino-piperidin-1-yl)-xanthine which is an oral daily dose of from 2.5 mg to 10 mg, and a pharmaceutically effective amount of metformin.

19. A method of treating type II diabetes mellitus comprising administering to a patient in need thereof a pharmaceutically effective oral amount of 1-[(4-methyl-quinazolin-2-yl)- methyl]-3-methyl-7-(2-butyn-1-yl)-8-(3-(R)-amino-piperidin-1-yl)-xanthine which is an oral daily dose of 5 mg, and a pharmaceutically effective amount of metformin.

20. A method of treating type 2 diabetes or pre-diabetes comprising administering to a patient in need thereof a therapeutically effective oral dose of 1-[(4-methyl-quinazolin-2-yl)methyl]-3-methyl-7-(2-butyn-1-yl)-8-(3-(R)-amino-piperidin-1-yl)-xanthine in combination with a therapeutically effective dose of metformin, wherein the 1-[(R4-methyl-quinazolin-2-yl)-methyl]-3-methyl-7-(2-butyn-1-yl)-8-(3-(R)-amino-piperidin-1-yl)-xanthine is administered in an oral dosage of from 0.5 mg to 50 mg.

21. The method according to claim 20, wherein the 1-[(4-methyl-quinazolin-2-yl)-methyl]-3-methyl-7-(2-butyn-1-yl)-8-(3-(R)-amino-piperidin-1-yl)-xanthine is administered in an oral dosage of from 2.5 mg to 50 mg.

22. The method according to claim 20, wherein the 1-[(4-methyl-quinazolin-2-yl)-methyl]-3-methyl-7-(2-butyn-1-yl)-8-(3-(R)-amino-piperidin-1-yl)-xanthine is administered in an oral dosage of from 2.5 mg to 10 mg.

23. The method according to claim 20, wherein the 1-[(4-methyl-quinazolin-2-yl)-methyl]-3-methyl-7-(2-butyn-1-yl)-8-(3-(R)-amino-piperidin-1-yl)-xanthine is administered in an oral dosage of 0.5 mg, 1 mg, 2.5 mg, 5 mg or 10 mg.

24. The method according to claim 20, wherein the 1-[(4-methyl-quinazolin-2-yl)-methyl]-3-methyl-7-(2-butyn-1-yl)-8-(3-(R)-amino-piperidin-1-yl)-xanthine is administered in an oral dosage of 1 mg, 2.5 mg or 5 mg.

25. The method according to claim 20, wherein the 1-[(4-methyl-quinazolin-2-yl)-methyl]-3-methyl-7-(2-butyn-1-yl)-8-(3-(R)-amino-piperidin-1-yl)-xanthine is administered in an oral dosage of 2.5 mg or 5 mg.

26. The method according to claim 20, wherein the 1-[(4-methyl-quinazolin-2-yl)-methyl]-3-methyl-7-(2-butyn-1-yl)-8-(3-(R)-amino-piperidin-1-yl)-xanthine is administered in an oral daily dose of 5 mg.

* * * * *